(12) United States Patent
Robertson et al.

(10) Patent No.: US 12,352,695 B2
(45) Date of Patent: *Jul. 8, 2025

US012352695B2

(54) SYSTEM AND METHOD FOR MONITORING THE HEALTH OF DIALYSIS PATIENTS

(71) Applicant: Virginia Tech Intellectual Properties, Inc., Blacksburg, VA (US)

(72) Inventors: John L. Robertson, Floyd, VA (US); Ryan Senger, North Chesterfield, VA (US); Pang Du, Blacksburg, VA (US)

(73) Assignee: Virginia Tech Intellectual Properties, Inc., Blacksburg, VA (US)

( * ) Notice: Subject to any disclaimer, the term of this patent is extended or adjusted under 35 U.S.C. 154(b) by 0 days.

This patent is subject to a terminal disclaimer.

(21) Appl. No.: 18/122,180

(22) Filed: Mar. 16, 2023

(65) Prior Publication Data

US 2023/0243752 A1 Aug. 3, 2023

Related U.S. Application Data

(63) Continuation of application No. 15/305,940, filed as application No. PCT/US2015/027323 on Apr. 23, 2015, now Pat. No. 11,674,903.

(60) Provisional application No. 61/983,038, filed on Apr. 23, 2014.

(51) Int. Cl.
| | |
|---|---|
| *G01N 21/65* | (2006.01) |
| *A61B 5/00* | (2006.01) |
| *A61B 5/145* | (2006.01) |
| *A61M 1/14* | (2006.01) |
| *A61M 1/16* | (2006.01) |
| *A61M 1/28* | (2006.01) |
| *A61M 1/36* | (2006.01) |
| *G01N 33/49* | (2006.01) |
| *G16H 10/40* | (2018.01) |
| *G16H 20/40* | (2018.01) |

(52) U.S. Cl.
CPC .......... *G01N 21/65* (2013.01); *A61B 5/0075* (2013.01); *A61B 5/14525* (2013.01); *A61B 5/6866* (2013.01); *A61M 1/14* (2013.01); *A61M 1/1609* (2014.02); *A61M 1/1619* (2014.02); *A61M 1/1692* (2013.01); *A61M 1/282* (2014.02); *A61M 1/3609* (2014.02); *G01N 33/492* (2013.01); *G16H 10/40* (2018.01); *G16H 20/40* (2018.01); *A61M 2205/3313* (2013.01); *A61M 2205/50* (2013.01); *A61M 2205/52* (2013.01); *G01N 21/658* (2013.01); *G01N 2570/00* (2013.01)

(58) Field of Classification Search
CPC ... A61M 1/1619; G01N 21/65; G01N 33/492; A61B 5/0075; A61B 5/6866
See application file for complete search history.

(56) References Cited

U.S. PATENT DOCUMENTS

| | | |
|---|---|---|
| 3,598,727 A | 8/1971 | Willock |
| 4,172,033 A | 10/1979 | Willock |
| 4,267,040 A | 5/1981 | Schal |
| 4,769,134 A | 9/1988 | Allan et al. |
| 5,112,127 A | 5/1992 | Carrabba et al. |
| 5,507,723 A | 4/1996 | Keshaviah |
| 5,534,997 A | 7/1996 | Schrader |
| 5,553,616 A | 9/1996 | Ham et al. |
| 5,786,893 A | 7/1998 | Fink et al. |
| 6,100,975 A | 8/2000 | Smith et al. |
| 6,151,522 A | 11/2000 | Alfano et al. |
| 6,284,131 B1 | 9/2001 | Hogard et al. |
| 6,632,680 B1 | 10/2003 | Deslauriers et al. |
| 7,326,576 B2 | 2/2008 | Womble et al. |
| 7,505,128 B2 | 3/2009 | Zribi et al. |
| 7,524,671 B2 | 4/2009 | Clarke et al. |

(Continued)

FOREIGN PATENT DOCUMENTS

| | | |
|---|---|---|
| EP | 1637586 A2 | 3/2006 |
| WO | 2007011571 A2 | 1/2007 |

(Continued)

OTHER PUBLICATIONS

Jensen et al. "Online monitoring of urea concentration in dialysate with dual-beam Fourier-transform near-infrared spectroscopy." Journal of Biomedical Optics 9.3 (2004): 553-557. (Year: 2004).*
Co-pending international Application No. PCT/US2015/027323 International Search Report and Written Opinion dated Sep. 8, 2015, 11 pages.
Das, R.S. and Agrawal, Y.K. "Raman spectroscopy: Recent advancements, techniques and applications". Vib. Spectrosc. 2011. 57(2): 163-176, Abstract only.

(Continued)

*Primary Examiner* — Emily A Cordas
(74) *Attorney, Agent, or Firm* — New River Valley IP Law, P.C.; Michele L. Mayberry; Ashley M. Gates

(57) ABSTRACT

A system and method for monitoring the health of dialysis patients with Raman spectroscopy measurements of one or more target analytes is described. The methods include irradiating one or more fluids of interest with light to produce one or more spectrum and detecting the spectrum with a detector. The fluids of interest are preferably those related to dialysis, including hemodialysis and peritoneal dialysis. In a preferred embodiment, the fluids are irradiated with monochromatic light, and one or more Raman spectra are detected as a result of the irradiation. The fluids may be irradiated within the dialysis tubing itself, or removed from the dialysis tubing and irradiated in a separate chamber. The Raman spectra of one or more target analytes of a dialysis patient may be followed over time or compared to one or more reference spectra, thereby providing information on the health of dialysis patients.

12 Claims, 22 Drawing Sheets

(56) References Cited

U.S. PATENT DOCUMENTS

| | | |
|---|---|---|
| 7,651,851 B2 | 1/2010 | Clarke et al. |
| 8,125,623 B2 | 2/2012 | Munger et al. |
| 8,133,194 B2 | 3/2012 | Szamosfalvi et al. |
| 8,638,431 B2 | 1/2014 | Ashok et al. |
| 8,699,020 B1 | 4/2014 | Zhou et al. |
| 8,945,936 B2 | 2/2015 | Ash et al. |
| 8,953,159 B2 | 2/2015 | Cunningham et al. |
| 9,089,126 B2 | 7/2015 | Faulkner et al. |
| 9,215,985 B2 | 12/2015 | Gross et al. |
| 9,267,845 B2 | 2/2016 | Ichijyo et al. |
| 9,550,020 B2 | 1/2017 | Kelly et al. |
| 9,713,666 B2 | 7/2017 | Pudil et al. |
| 11,324,869 B2 | 5/2022 | Robertson et al. |
| 11,674,903 B2 | 6/2023 | Robertson et al. |
| 2006/0281068 A1 | 12/2006 | Maier et al. |
| 2007/0109535 A1 | 5/2007 | Maier et al. |
| 2008/0015487 A1* | 1/2008 | Szamosfalvi ....... A61M 1/3413 210/323.1 |
| 2008/0097272 A1 | 4/2008 | Daniel et al. |
| 2008/0158544 A1 | 7/2008 | Womble et al. |
| 2010/0070197 A1 | 3/2010 | Wang et al. |
| 2010/0165324 A1 | 7/2010 | Womble et al. |
| 2012/0008130 A9 | 1/2012 | Munger et al. |
| 2012/0099102 A1 | 4/2012 | Bello |
| 2012/0276549 A1 | 11/2012 | Cunningham et al. |
| 2013/0056418 A1 | 3/2013 | Kopperschmidt et al. |
| 2014/0052386 A1 | 2/2014 | Guenther et al. |
| 2014/0098359 A1 | 4/2014 | Gross et al. |
| 2016/0252459 A1 | 9/2016 | Bell et al. |
| 2017/0045455 A1 | 2/2017 | Robertson et al. |
| 2021/0215610 A1 | 7/2021 | Robertson et al. |
| 2021/0270742 A1 | 9/2021 | Senger et al. |
| 2021/0389251 A1 | 12/2021 | Robertson et al. |
| 2022/0040390 A1 | 2/2022 | Robertson et al. |
| 2023/0147592 A1 | 5/2023 | Robertson et al. |

FOREIGN PATENT DOCUMENTS

| | | |
|---|---|---|
| WO | 2012140022 A1 | 10/2012 |
| WO | 2015164620 A1 | 10/2015 |
| WO | 2016004322 A2 | 1/2016 |
| WO | 2020176663 A1 | 9/2020 |

OTHER PUBLICATIONS

Dator, R. et al., "Metabolomics profiles of smokers from two ethnic groups with differing lung cancer risk", Chem. Res. Toxicol. 2020; 33(8):2087-2098.

Daugirdas, John T. et al. "Improved equation for estimating single-pool Kt/V at higher dialysis frequencies", Nephrol Dial Transplant (2013) 28: 2156-2160.

Daugirdas, John T. et al. "Surface-Area-Normalized Kt/V: A Method of Rescaling Dialysis Dose to Body Surface Area-Implications for Different-Size Patients by Gender", Semin Dial. 2008; 21(5): 415-421, 17 pages.

Depciuch, J. et al. "Application of Raman Spectroscopy and Infrared Spectroscopy in the Identification of Breast Cancer". Appl. Spectrosc. 2016. 70(2): 251-263.

Dobre, M, Meyer, TW, Hostetter, TH, "Searching for uremic toxins," Clin J Am Soc Nephrol 8: 322-327, 2013.

Duranton, F et al., "Normal and pathological concentrations of uremic toxins," J Am Soc Nephrol 23: 1258-1270, 2012.

Eilers, P.H.C. "A perfect smoother". Anal. Chem. 2003. 75(14): 3631-3636, Abstract only.

Eknoyan, G. et al., "Effects of dialysis dose and membrane flux in maintenance hemodialysis," New Engl Journ Med 347: 2010-2019, 2002.

Emwas, A. H. et al., "Standardizing the experimental conditions for using urine in NMR-based metabolomic studies with a particular focus on diagnostic studies: a review", Metabolomics 2015; 11(4):872-894.

Fisher, A.K. et al. "The RametrixTM LITE Toolbox v1.0 for Mathlab®". J. Raman Spectrosc. 2018, 49(5): 885-896, Abstract only.

Fisher, M. et al., "AKI in hospitalized patients with and without COVID-19: A comparison study", J. Am. Soc. Nephrol. 2020; 31: 2145-2157.

Gautam, R. et al. "Review of multidimensional data processing approaches for Raman and infrared spectroscopy". EPJ Techn. Instrum. 2015. 2(1): 8, 38 pages.

Gowda, G. A. et al., "Metabolomics-based methods for early disease diagnostics", Expert Rev. Mol. Diagn. 2008; 8(5):617-633, 28 pages.

Hassler, L. et al., "Evidence for and against direct kidney infection by SARS-CoV-2 in patients with COVID-19", CJASN 2021; 16, 1755-1765, 2021.

He, S. et al. "Baseline correction for Raman spectra using an improved asymmetric least squares method". Anal. Methods. The Royal Society of Chemistry, 2014. 6(12): 4402-4407.

Hirsch, J. S. et al., "Acute kidney injury in patients hospitalized with COVID-19", Kidney Int. 2020; 98: 209-218.

Huttanus, H. et al. "Raman Chemometric Urinalysis (Rametrix™) as a screen for bladder cancer," PLoS One. 2020; 15(8): e0237070. Published online Aug. 21, 2020.

Hyde, F.W. et al., "Detection of antigens in urine of mice and humans infected with Borrelia burgdorferi, etiologic agent of Lyme disease," J Clin Microbiol 27, 58-61 (1989).

Ito, S, Yoshida, M, "Review: Protein-bound uremic toxins: new culprits of cardiovascular events in chronic kidney disease patients," Toxins 6: 665-678, 2014; doi:10.3390/toxins6020665.

Jha, V. et al., "Chronic kidney disease: global dimension and perspectives", The Lancet, 2013, 382(9888), 260-272.

Kerr, L.T. et al., Methodologies for bladder cancer detection with Raman based urine cytology. Analytical Methods, 2016;8: 4991-5000, Abstract only.

Kim, Jaejin et al., "Feasibility Study for the Monitoring of Urea in Dialysate Solution using Raman Spectroscopy", Bull. Korean Chem. Soc. 2011, vol. 32, No. 3 805-808.

Lafuente, B. et al.,"The power of databases: the RRUFF project". In: T. Armbruster, R.M. Danisi, editors. Highlights in Mineralogical Crystallography. W. De Gruyter, Berlin, Germany, 2015, 32 pages.

Lee, S. et al., "Improving Clearance for Renal Replacement Therapy", Kidney 360 Publish Ahead of Print, published May 12, 2021, 32 pages.

Levey, AS et al., "Controlling the epidemic of cardiovascular disease in chronic renal disease: What do we need to learn? Where do we go from here?," Amer J Kid Disease 32: 853-906, 1998.

Li, J. et al. "Wavelet transform based on the optimal wavelet pairs for tunable diode laser absorption spectroscopy signal processing". Appl. Spectrosc. 2015. 69(4): 496-506.

Liabeuf, S, Drukke, TB, Massay, ZA, "Protein-bound uremic toxins: new insight from clinical studies," Toxins 3: 911-919, 2011.

Lieber, C.A. and Mahadevan-Jansen, A. "Automated Method for Subtraction of Fluorescence from Biological Raman Spectra". Appl. Spectrosc. 2003. 57: 1363-1367, Abstract only.

Liland, K. et al. "Model-based pre-processing in Raman spectroscopy of biological samples". J. Raman Spectrosc. 2016. 47(6): 643-650.

Liland, K. et al. "Optimal Choice of Baseline Correction for Multivariate Calibration of Spectra" Appl. Spectrosc. 2010, 64: 1007-1016.

Liu, J. et al. "Goldindec: A Novel Algorithm for Raman Spectrum Baseline Correction". Appl. Spectrosc. 2015. 69(7): 834-842.

Lo, P.A. et al., Automatic Raman spectroscopic urine crystal identification system using fluorescent image-guided 2D scanning platform with Fe3O4 crystal violet nanoclusters. J Raman Spectrosc 2018;50(1)34-50, Abstract only.

Magni, R. et al., "Application of Nanotrap technology for high sensitivity measurement of urinary outer surface protein A carboxyl terminus domain in early stage Lyme borreliosis," J Transl Med (2015) 13: 346, 22 pages.

Mahadevan-Jansen, A. and Richards-Kortum, R.R. "Raman spectroscopy for the detection of cancers and precancers". J. Biomed. Opt. 1996. 1(1): 31-70.

(56) References Cited

OTHER PUBLICATIONS

Martens, H. and Stark, E. "Extended multiplicative signal correction and spectral interference subtraction: new preprocessing methods for near infrared spectroscopy." J. Pharm. Biomed. Anal. 1991. 9 8: 625-635, Abstract only.
Mazet, V. et al. "Background removal from spectra by designing and minimising a non-quadratic cost function". Chemom. Intell. Lab. Syst. 2005. 76(2): 121-133.
Meyer, T. W. et al., "Dialysis Cannot be Dosed", Semin Dial. 2011; 24(5): 471-479, 19 pages.
Meyer, TW, Hostetter, TH, "Uremia", New Engl J Med 357: 1316-1325, 2007.
Minka "A statistical learning/pattern recognition glossary." Retrieved Jun. 29, 2005: 2008. Available online http://alumni.media.mit.edu/~tpminka/statlearn/glossary/glossary.htm., accessed Jul. 1, 2020 (Year: 2005).
Mohamed, M. M. et al., "Acute kidney injury associated with coronavirus disease 2019 in urban New Orleans", Kidney360 2020; 1: 614-622, 19 pages.
Moledina, D. G. et al., "The association of COVID-19 with acute kidney injury independent of severity of illness: A multicenter cohort study", Am. J. Kidney Dis. 2021; 77: 490-499.e1, 12 pages.
Mosier-Boss, P.A. et al. "Fluorescence rejection in Raman spectroscopy by shifted-spectra, edge detection, and FFT filtering techniques". Appl. Spectrosc. 1995. 49: 630-638.
Movasaghi, Z. et al., Raman Spectroscopy of Biological Tissues. Appl Spectrosc Rev. 2007;42: 493-541.
Murugan, R. and Kellum, J. A., "Acute kidney injury: what's the prognosis?" Nat. Rev. Nephrol. 2011; 7(4): 209-217.
Ng, J. H. et al., "Pathophysiology and pathology of acute kidney injury in patients with COVID-19", Adv. Chronic Kidney Dis. 2020; 27: 365-376.
Pegalajar-Jurado, A. et al., (2018) "Identification of urine metabolites as biomarkers of early Lyme Disease," Nature Scientific Reports 8:12204, 12 pages.
Pei, G. et al., "Renal involvement and early prognosis in patients with COVID-19 pneumonia", J. Am. Soc. Nephrol. 2020; 31: 1157-1165.
Peng, J. et al. "Asymmetric least squares for multiple spectra baseline correction". Anal. Chim. Acta. 2010. 683(1):63-68.
Beattie, J. Renwick et al. "Prediction of Adipose Tissue Composition Using Raman Spectroscopy: Average Properties and Individual Fatty Acids", 2006, 8 pages.
Bispo, J. et al. "Correlating the amount of urea, creatinine, and glucose in urine from patients with diabetes mellitus and hypertension with the risk of developing renal lesions by means of Raman spectroscopy and principal component analysis", Journal of Biomedical Optics 18(8), 087004 (Aug. 2013), 8 pages.
Bonifacio, A. et al. Label-free surface-enhanced Raman spectroscopy of biofluids: fundamental aspects and diagnostic applicants, Anal. Bioanal. Chem. (2015) 407:8265-8277, 13 pages.
Co-Pending U.S. Appl. No. 17/146,301, Applicant-Initiated Interview Summary dated Jan. 25, 2024, 3 pages.
Co-Pending U.S. Appl. No. 17/146,301, Final Office Action dated Mar. 21, 2024, 33 pages.
Co-Pending U.S. Appl. No. 17/146,301, Non-final Office Action dated Jun. 13, 2023, 27 pages.
Co-Pending U.S. Appl. No. 17/146,301, Response to Jun. 13, 2023 Non-final Office Action, dated Dec. 12, 2023, 21 pages.
Co-Pending U.S. Appl. No. 17/146,301, Supplemental Amendment dated Mar. 4, 2024, 12 pages.
Co-pending U.S. Appl. No. 17/345,735, Non-Final Office Action dated Jun. 14, 2023, 15 pages.
Co-pending U.S. Appl. No. 17/345,735, Notice of Allowance dated Dec. 1, 2023, 7 pages.
Co-pending U.S. Appl. No. 17/345,735, Response to Jun. 14, 2023 Non-Final Office Action, dated Nov. 14, 2023, 8 pages.
Del Mistro, G. et al. "Surface-enhanced Raman spectroscopy of urine for prostate cancer detection: a preliminary study", Analytical Bioanalytical Chemistry, 407, 3271-3275, 2015.
Fisher, A. K. et al. "Raman Chemometrics and Application to Enzyme Kinetics and Urinalysis" [Doctoral dissertation, Virginia Tech], 142 pages, , 2018.
Schena, F. P. Management of patients with chronic kidney disease, Intern Emerg Med (2011) 6, 7 pages.
Thermo Fisher Scientific, "DXR SmartRaman Spectrometer", 2017, 8 pages.
Van Rhijn, B. W. G. et al. Urine Markers for Bladder Cancer Surveillance: A Systematic Review, European Urology 47 (2005) 736-748.
Webster, A. C. et al. Chronic kidney disease. The lancet, 389(10075), 2017, pp. 1238-1252.
Xu and Du, (Jul. 27-Aug. 1, 2019). ISREA:A Novel Approach for Raman Spectrum Baseline Correction and Its Application on Real Data [abstract]. JSM 2019, Denver, CO. [Retrieved online Nov. 14, 2023] (Year: 2019).
Rauter, C. et al., "Critical evaluation of urine-based PCR assay for diagnosis of Lyme borreliosis," Clin Diagn Lab Immunol 12: 910-917 (2005).
Richardson, S. et al., "Presenting characteristics, comorbidities, and outcomes among 5700 patients hospitalized with COVID-19 in the New York City area", JAMA 2020; 323: 2052-2059.
Robertson, J. L. et al. (2022), "Alterations in the molecular composition of COVID-19 patient urine, detected using Raman spectroscopic/computational analysis", PLOS ONE 17(7): e0270914, 16 pages.
Scholtes-Timmerman, M. et al. "A novel approach to correct variations in Raman spectra due to photo-bleachable cellular components". Analyst. 2009. 134(2): 387-393.
Schulze, G. et al. "Investigation of selected baseline removal techniques as candidates for automated implementation". Appl. Spectrosc. 2005. 59(5): 545-574.
Senger, R.S. and Robertson, J.L. "The RametrixTM Pro Toolbox v1.0 for Matlab®". PeerJ. 2020. 8: e8179.
Senger, R.S. and Scherr, D., "Resolving complex phenotypes with Raman spectroscopy and chemometrics", Curr. Opin. Biotechnol. 2020; 66:277-282, 16 pages.
Senger, R.S. et al. "Spectral characteristics of urine from patients with end-stage kidney disease analyzed using Raman Chemometric Urinalysis (Rametrix)". PLoS One. 2020. 15(1): e0227281).
Senger, R.S. et al. "Spectral characteristics of urine specimens from healthy human volunteers analyzed using Raman chemometric urinalysis (Rametrix)". PLoS One. 2019. 14(9): e0222115.
Shapiro, A. et al., Raman molecular imaging: a novel spectroscopic technique for diagnosis of bladder cancer in urine specimens. Eur Urol. 2011;59: 106-112.
Sharma, P. et al., "COVID-19-associated kidney injury: A case series of kidney biopsy findings", J. Am. Soc. Nephrol. 2020; 31: 1948-1958.
Shen, Y. et al., "Raman imaging of small biomolecules", Annu. Rev. Biophys. 2019; 48:347-369.
Shinzawa, H. et al., "Multivariate data analysis for Raman spectroscopic imaging" Journal of Raman Spectroscopy, 2009, 40:1720-1725.
Shusterman, V. et al. "Enhancing the precision of ECG baseline correction: selective filtering and removal of residual error". Comput. Biomed. Res. 2000. 33(2): 144-160, Abstract only.
Stellman, C.M. et al. "Multivariate Raman Imaging of Simulated and Real World Glass-Reinforced Composites". Appl. Spectrosc. 1996. 50: 552-557, Abstract only.
Su, H. et al., "Renal histopathological analysis of 26 postmortem findings of patients with COVID-19 in China", Kidney Int. 2020; 98: 219-227.
Turi, K. N. et al., "A review of metabolomics approaches and their application in identifying casual pathways of childhood asthma", J. Allergy Clin. Immunol. 2018; 141(4):1191-1201, 48 pages.
Vanholder, R, et al., European Uremic Toxin Work Group (EUTox), "Review on uremic toxins: classification, concentration, and interindividual variability," Kidney Int. May 2003;63(5):1934-43, 2003.
Wang, N. et al. "Recent advances in spontaneous Raman spectroscopic imaging: Instrumentation and applications" Current Medici-

(56) References Cited

OTHER PUBLICATIONS nal Chemistry, vol. 27, No. 36, 2020, pp. 6188-6207(20), Available online Jul. 26, 2019, Abstract only.
Ward, R. A. et al., "Dialysate Flow Rate and Delivered Kt/Vurea for Dialyzers with Enhanced Dialysate Flow Distribution", Clin J Am Soc Nephrol 6: 2235-2239, Sep. 2011.
Xu, Y. et al., "Sparse logistic regression on functional data", Stat. Interface, vol. 0 (2021) 1, 9 pages.
Yang, Y.T. et al., Off-Resonance SERS Nanoprobe-Targeted Screen of Biomarkers for Antigens Recognition of Bladder Normal and Aggressive Cancer Cells. Analytical Chemistry 2019;91(13): 8213-8220.
Zhang, D. and Ben-Amotz, D. "Enhanced Chemical Classification of Raman Images in the Presence of Strong Fluorescence Interference". Appl. Spectrosc. OSA, 2000, 54(9): 1379-1383, Abstract only.
Zhao, J. et al. "Automated autofluorescence background subtraction algorithm for biomedical Raman spectroscopy". Appl. Spectrosc. 2007. 61(11): 1225-1232, Abstract only.
Zu, T.N.K. et al., Assessment of ex vivo Perfused Liver Health by Raman Spectroscopy. J Raman Spectrosc. 2015; 46: 551-558, Abstract only.
Zu, T.N.K. et al., Near-Real-Time Analysis of the Phenotypic Responses of *Escherichia coli* to 1-Butanol Exposure Using Raman Spectroscopy. J Bacteriol. 2014;196: 3983-3991.
Afseth, N.K. and Kohler, A. "Extended multiplicative signal correction in vibrational spectroscopy, a tutorial". Chemometrics and Intelligent Laboratory Systems. 2012. 117: 92-99. 10.1016/j.chemolab.2012.03.004, Abstract only.
Athamneh, A.I.M. and Senger R.S. Peptide-Guided Surface-Enhanced Raman Scattering Probes for Localized Cell Composition Analysis. Appl Env Microbiol. 2012;78: 7805-7808.
Athamneh, A.I.M. et al., Phenotypic Profiling of Antibiotic Response Signatures in *Escherichia coli* Using Raman Spectroscopy. Antimicrob Agents Chemother. 2014;58: 1302-1314.
Balan et al. "Vibrational spectroscopy fingerprinting in medicine: from molecular to clinical practice." Materials 12.18 (2019): 2884, 40 pages.
Batlle, D. et al. "Acute Kidney Injury in COVID-19: Emerging Evidence of a Distinct Pathophysiology", J. Am. Soc. Nephrol. 2020; 31: 1380-1383.
Beattie, J.R. and McGarvey, J.J. "Estimation of signal backgrounds on multivariate loadings improves model generation in face of complex variation in backgrounds and constituents". J of Raman Spectrosc. 2013. 44(2): 329-338. 10.1002/jrs.4178, Abstract only.
Bird, B. et al., Cytology by Infrared Micro-Spectroscopy: Automatic Distinction of Cell Types in Urinary Cytology. Vib Spectrosc. 2008;48: 101-106, 15 pages.
Bouatra, S. et. al. The Human Urine Metabolome. PLOS ONE. 2013;8: e73076, 25 pages.
Cai, T.T. et al. "Enhanced Chemical Classification of Raman Images Using Multiresolution Wavelet Transformation". Appl. Spectrosc. 2001. 55(9): 1124-1130.
Cai, Y. et al. "Baseline correction for Raman spectra using penalized spline smoothing based on vector transformation". Anal. Methods. 2018. 10(28): 3525-3533, Abstract only.
Candeloro, P. et al. "Raman database of amino acids solutions: A critical study of extended multiplicative signal correction". Analyst. 2013. 138(24): 7331-7340).
Canetta, E. et al., Modulated Raman spectroscopy for enhanced identification of bladder tumor cells in urine samples. J Biomed Opt. 2011;16(3): 037002, 8 pages.
Castelli, F. A. et al., "Metabolomics for personalized medicine: the input of analytical chemistry from biomarker discovery to point-of-care tests", Anal. Bioanal. Chem. 414, 759-789 (2022).
Centers for Disease Control and Prevention, National Chronic Kidney Disease Factsheet, 2014, 4 pages.
Chen, D. et al. "Adaptive wavelet transform suppresses background and noise for quantitative analysis by Raman spectrometry". Anal. Bioanal. Chem. 2011. 400(2): 625-634, Abstract Only.
Chen, Y. T. et al., "Mortality rate of acute kidney injury in SARS, MERS, and COVID-19 infection: A systematic review and meta-analysis", Crit. Care 2020; 24: 439, 4 pages.
Chen, Z. and Kim, J. "Urinary proteomics and metabolomics studies to monitor bladder health and urological diseases", BMC Urol. 2016; 16 (Mar. 22): 11, 13 pages.
Cheng, S. et al., "Potential impact and study considerations of metabolomics in cardiovascular health and disease: A scientific statement from the American Heart Association", Circ. Cardiobasc. Genet. 2017; 10(2): e000032, 13 pages.
Cheng, Y. et al., "Kidney disease is associated with in-hospital death of patients with COVID-19", Kidney Int. 2020; 97: 829-838.
Chiu, Y.C. et al., Enhanced Raman sensitivity and magnetic separation for urolithiasis detection using phosphonic acid-terminated $Fe_3O_4$ nanoclusters. J. Mater. Chem. B 2015(3):4282-4290.
Collins, AJ et al., "Death, hospitalization, and economic associations among incident hemodialysis patients with hematocrit values of 36 to 39%," J Am Soc Nephrol 12(11):2465-73, 2001.
Co-pending U.S. Appl. No. 15/305,940, Applicant-Initiated Interview Summary dated Mar. 28, 2022, 3 pages.
Co-pending U.S. Appl. No. 15/305,940, Applicant-Initiated Interview Summary, dated Jan. 18, 2023, 4 pages.
Co-pending U.S. Appl. No. 15/305,940, Final Office Action dated Dec. 1, 2021, 27 pages.
Co-pending U.S. Appl. No. 15/305,940, Final Office Action dated Dec. 22, 2022, 18 pages.
Co-pending U.S. Appl. No. 15/305,940, Final Office Action dated Jul. 13, 2020, 22 pages.
Co-pending U.S. Appl. No. 15/305,940, Non-Final Office Action dated Jun. 2, 2022, 37 pages.
Co-pending U.S. Appl. No. 15/305,940, Non-Final Office Action dated May 7, 2021, 24 pages.
Co-pending U.S. Appl. No. 15/305,940, Non-Final Office Action dated Nov. 1, 2019, 16 pages.
Co-pending U.S. Appl. No. 15/305,940, Notice of Allowance dated Feb. 1, 2023, 7 pages.
Co-pending U.S. Appl. No. 15/305,940, Response After Final Office Action, dated Jan. 13, 2023, 6 pages.
Co-pending U.S. Appl. No. 15/305,940, Response to Dec. 1, 2021 Final Office Action, dated Feb. 25, 2022, 17 pages.
Co-pending U.S. Appl. No. 15/305,940, Response to Jul. 13, 2020 Final Office Action, filed Oct. 13, 2020, 11 pages.
Co-pending U.S. Appl. No. 15/305,940, Response to Jun. 2, 2022 Non-Final Office Action, dated Dec. 2, 2022, 31 pages.
Co-pending U.S. Appl. No. 15/305,940, Response to Mar. 27, 2019 Restriction Requirement, filed Sep. 27, 2019, 9 pages.
Co-pending U.S. Appl. No. 15/305,940, Response to May 7, 2021 Non-Final Office Action, filed Sep. 7, 2021, 14 pages.
Co-pending U.S. Appl. No. 15/305,940, Response to Nov. 1, 2019 Non-Final Office Action, filed May 1, 2020, 13 pages.
Co-pending U.S. Appl. No. 15/305,940, Restriction Requirement dated Mar. 27, 2019, 9 pages.
Co-pending U.S. Appl. No. 15/305,940, Rule 132 Affidavit dated Dec. 2, 2022, 23 pages.
Co-Pending U.S. Appl. No. 17/146,301, Response to Notice to File Corrected Application Papers filed Feb. 8, 2021, 228 pages.
Co-pending U.S. Appl. No. 17/434,294, Notice of Allowance dated Dec. 29, 2021, 11 pages.
Co-pending International Application No. PCT/US20/19964, International Search Report and Written Opinion dated May 22, 2020, 7 pages.
Co-Pending U.S. Appl. No. 17/146,301, Response to Mar. 21, 2024, Final Office Action dated Aug. 21, 2024, 74 pages.

\* cited by examiner

|  | Patient 1 | Patient 2 | Patient 3 | Patient 4 | Patient 5 | Patient 6 |
|---|---|---|---|---|---|---|
| Gender | Male | Male | Female | Female | Male | Female |
| Stable/Unstable | Stable | Stable | Stable | Stable | Stable | Stable |
| IHD Total Time | < 6 months | > 6 months | > 4 years | <2 months | 1st tx of IHD | <6 Months |
| Challenges | N/A | Challenge in achieving EDW due to cardiac function | N/A | N/A | Previous PD patient – 1st hemo tx | N/A |
| Treatment Time | 4hrs 4min | 3hrs 48min | 3hrs 41min | 3hrs 51min | 3hrs 58min | 4hrs 2min |
| Dialysate | G2231 2.0K, 2.25Ca, 1.0Mg, 100 Dextrose | G2231 2.0K, 2.25Ca, 1.0Mg, 100 Dextrose | G2231 2.0K, 2.25CA, 1.0Mg, 100 Dextrose | G2231 2.0K, 2.25Ca, 1.0Mg, 100 Dextrose | G2231 2.0K, 2.25Ca, 1.0Mg, 100 Dextrose | G2231 2.0K, 2.25Ca, 1.0Mg, 100 Dextrose |
| Days Between Last Treatment | 2 days | 2 days | 2 days | 2 days | 1st Hemo In-Center – 3 days | 2 days |
| Last Meal | Unable to obtain – when asked pt states normally does not eat until after tx | Unable to obtain – when asked pt states normally does not eat before tx – has nutritional drink during tx | Unable to obtain – when asked pt states that she normally has breakfast prior to tx and is usually whatever husband fixes | Unable to obtain – when asked pt states it varies if she eats prior to tx | Unable to obtain – Pt is no longer on dialysis – pt chose to sign off | Unable to obtain – when asked pt states she usually eats during dialysis |
| Albumin | 3.5 | 4.1 | 4.5 | 3.1 | 3.2 | 3.8 |
| Dialyzer Type | 160NRe Optiflux - High flux | 160NRe Optiflux – High flux | 160NRe Optiflux – High Flux | 180NRe Optiflux – High Flux | 160NRe Optiflux – High Flux | 180NRe Optiflux – High Flux |
| Hyperglycemic | 267 | N/A | N/A | No result found | N/A | N/A |

FIG. 5

SYSTEM AND METHOD FOR MONITORING THE HEALTH OF DIALYSIS PATIENTS

CROSS-REFERENCE TO RELATED APPLICATIONS

This application is a Continuation application of U.S. patent application Ser. No. 15/305,940, filed Oct. 21, 2016. The '940 application is a National Stage application under 35 USC § 371 of International Application No. PCT/US15/27323, filed Apr. 23, 2015, which application relies on the disclosure of and claims priority to and the benefit of the filing date of U.S. Provisional Application No. 61/983,038, filed on Apr. 23, 2014, the disclosures of each of which are hereby incorporated by reference herein in their entireties.

BACKGROUND OF THE INVENTION

Field of the Invention

The present invention relates to the field of clinical care of dialysis and kidney transplant patients. More particularly, the present invention relates to a system and method for monitoring the health of dialysis and kidney transplant patients with Raman spectroscopy measurements of one or more target analytes.

Description of Related Art

Kidney disease is prevalent and can lead to both acute and chronic renal failure and to end-stage renal disease (ESRD). The Centers for Disease Control and Prevention estimates that one in 10 Americans (more than 20 million people) are affected to some degree with chronic renal failure (National Kidney and Urologic Disease Information Clearinghouse, National Institutes of Diabetes, Digestive, and Kidney Diseases [NIDDK]). There is very high morbidity and mortality from ESRD. To put this in perspective, many of the more common forms of cancer have a better prospect for survival than ESRD. In addition, ESRD is a global problem ("ESRD patients in 2011: A global perspective," Fresenius Medical Corporation GmBH).

There are many causes of kidney disease, but some of the most common include inflammation (glomerulonephritis, pyelonephritis), cardiovascular disease, hypertension (high blood pressure), and diabetes mellitus (Centers for Disease Control and Prevention, National Chronic Kidney Disease Factsheet, 2014). Many kidney diseases are progressive diseases, beginning with relatively mild symptoms and manageable consequences that, with time, significantly damage and scar the kidneys. As people age, they experience more chronic kidney disease. With a continuing increase in the proportion of the elderly of the populations of all countries, the prevalence of chronic kidney disease will rise.

Patients who are in renal failure, due to acute disease or ESRD, require intensive medical therapy. Some cases of acute renal failure can be medically managed, but virtually all patients with ESRD require either dialysis or transplantation of a kidney to live. Worldwide (2011 data), it is estimated that there were 2,164,000 ESRD patients being treated with either hemodialysis (HD) or peritoneal dialysis (PD) ("ESRD patients in 2011: A global perspective," Fresenius Medical Corporation GmBH). Fresenius Medical Corporation estimates that the number of ESRD patients increases approximately 1-4% annually, due primarily to three factors: overall population growth, increase in lifespan due to old age (ESRD is more common), and increased incidence of diseases that cause ESRD (especially diabetes and hypertension) ("ESRD patients in 2011: A global perspective," Fresenius Medical Corporation GmBH).

In healthy people with normal renal function, the kidneys constantly remove a variety of metabolic waste products from the circulation. Examples of some waste product molecules are urea, formed during metabolism of proteins and amino acids, and creatinine, formed during remodeling of skeletal muscle cells. In fact, there are hundreds of waste products that are excreted through the kidney (and also the digestive tract). In people with renal failure, these waste products cannot be efficiently excreted, and they accumulate in the circulation, producing clinical signs of illness. The clinical syndrome "uremia" (literally "urine in the blood") is diagnosed when there is retention of excessive nitrogenous wastes in the circulation and other abnormalities related to renal failure, including dystrophic/metastatic calcification of soft tissues and demineralizing osteopathy (related to poor control of dietary calcium absorption and skeletal demineralization), anemia (the kidney makes the hormone erythropoietin), and anorexia, gastritis, gastric ulceration, pruritis/neuropathy, and pericarditis.

Some retained (unfiltered or unsecreted) waste molecules are collectively referred to as "uremic toxins." More than 80 molecules have been identified that as potential uremic toxins, which contribute to systemic morbidity associated with renal failure (Dobre, M, Meyer, T W, Hostetter, T H, "Searching for uremic toxins," Clin J Am Soc Nephrol 8:322327, 2013 ("Dobre et al., 2013"); Liabeuf, S, Drukke, T B, Massay, Z A, "Protein-bound uremic toxins: new insight from clinical studies," Toxins 3:911-919, 2011 doi: 10.3390/toxins3070911; Ito, S, Yoshida, M, "Review: Protein-bound uremic toxins: new culprits of cardiovascular events in chronic kidney disease patients," Toxins 6:665-678, 2014; doi: 10.3390/toxins6020665; and Duranton, F, Cohen, G, De Smet, R, Rodgiquez, M, Jankowski, J, Vanholder, R, Argiles, A, "Normal and pathological concentrations of uremic toxins," J Am Soc Nephrol 23:1258-1270, 2012. doi: 10.1681/ASN.2011121175 ("Duranton et al., 2012"). Many of these molecules are not removed well by either hemodialysis or peritoneal dialysis.

The primary goals of dialysis are reduction in the amount of circulating small molecular weight metabolic waste products, correction of plasma hydration, and systemic ion balancing (electrolytes, H+, $HCO3^-$, phosphate, among others). Reductions in small solute waste molecules and adjustment of the concentrations of water, ions, and pH, while not trivial, are usually accomplished well with current dialyzer membranes. These are small molecules and their movement between blood and dialysate is relatively predictable and controllable, based on flow, membrane characteristics, and duration/intensity of dialysis.

Hemodialysis (HD) is a therapeutic medical process during which metabolic impurities, such as the nitrogenous waste products of protein digestion and metabolism, are removed from the body of patients with renal failure. This is accomplished by selective filtration of plasma through semipermeable, engineered polymeric membranes. For HD treatment, the circulation of the patient is connected to a dialysis machine by way of an access cannula, usually in the patient's arm. Patient blood pressure, as well as a mechanical pump in the HD machine, circulates patient blood past a selectively porous membrane ("the dialyzer" or "coil"). The porous membrane of the dialyzer facilitates removal of small molecules, such as water, electrolytes, and small molecular weight nitrogenous wastes, primarily by processes of diffusion and osmosis. The blood of the patient remains on one side of the porous membrane and an aqueous fluid ("the dialysate") circulates on the other side. Concentration differences between molecules in the patient's circulation (high concentration of metabolic nitrogenous wastes, for example) and the dialysate (no nitrogenous wastes at the beginning of the cycle) osmotically draw waste products from the patient into the dialysate. The "patient contaminated" dialysate is constantly being discarded and replaced with fresh dialysate, providing the gradual removal of undesirable molecules from the circulation. HD patients gradually accumulate more metabolic wastes in their circulation over several days, requiring an HD treatment for several hours every few days. A typical HD patient is usually treated three or more times weekly, with 3-5 hours per treatment. A schematic simplified diagram of HD is shown in FIG. 1.

A second type of dialysis is peritoneal dialysis. In this type of treatment, a modified dialysate is infused into the peritoneal (abdominal) cavity of the patient with ESRD through a transabdominal, selectively porous catheter. Osmotic exchange of waste metabolites, such as urea, occurs across the thin membranes that cover the intestines and peritoneum. Periodically, the used dialysis fluids, with the dissolved waste metabolites, are drained and discarded.

Dialysis is a life-sustaining, temporary, maintenance medical therapy. It does not replace renal function and does not provide long-term patient survival. In reality, HD patients rarely survive more than 10 years and fewer than 40% survive more than 5 years. It is discouraging to note that the process of dialysis itself is dangerous and life-threatening. In virtually every age group studied, patients who undergo dialysis are more at risk of death than ESRD patients alone (not treated) or those treated with renal transplantation (Fink, J C, "Current outcomes for dialysis patients and improving quality of care for dialysis patients," in Principles and Practice of Dialysis, 4th ed., Henrich, W I (ed.) Wolters Kluwer/Lippincott, Williams and Wilkins, Philadelphia, 2009) ("Fink, 2009"). In this context, dialysis treatment is associated with higher mortality than medical management of ESRD. These data may not be completely representative, since dialysis patients, on average, may be more ill (thus requiring intensive medical intervention) than medically-managed ESRD patients.

The major cause of death in dialysis patients is cardiovascular disease. This includes death from sudden, catastrophic heart failure, myocardial infarction, cerebrovascular events, and segmental/diffuse cardiomyopathy (Levey A S, Beto J A, Coronado B E, Eknoyan G, Foley R N, Kasiske B I, Klag M J, Mailloux I U, Manske C I, Meyer K B, Parfrey P S, Pfeffer M A, Wenger N K, Wilson P W, Wright J T Jr. levey, A, Beto, JA, "Controlling the epidemic of cardiovascular disease in chronic renal disease: What do we need to learn? Where do we go from here?," Amer J Kid Disease 32:853-908, 1998; and Collins, A J, Li, S, St Peter, W, Ebben J, Roberts, T, Ma, J Z, Manning, W, "Death, hospitalization, and economic associations among incident hemodialysis patients with hematocrit values of 36 to 39%," J Am Soc Nephrol 12(11): 2465-73, 2001). Significant complications suffered directly as a result of the dialysis process (and indirectly from ESRD and co-morbidities causing ESRD) are anemia, skeletal demineralization and predisposition to pathologic fractures, failure/infection at the site of arteriovenous access, hemostatic abnormalities, abnormalities of drug effects/clearances, dyslipidemia, and altered acid-base homeostasis.

Taken together, this information indicates that although it is theoretically possible to maintain patients on dialysis for decades, in reality this does not occur. There could be many reasons for the disjunction between theoretical benefits of dialysis and the realities of outcomes (especially life expectancy), including that waste products of metabolism, that are detrimental to physiologic function, are not being sufficiently managed/cleared by current technology ("uremic toxins"); current methods for determining the dialysis needs of each patient (urea clearance-see below) may not accurately predict the actual dialysis needs of every patient; inadequate management of co-morbidities such as diabetes mellitus and hypertension; complications associated with, and failure of, of arteriovenous access; and/or complications of dialysis that alter patient physiology, including acid-base balance, hydration, ion trafficking, damage to formed elements of blood, and accumulation of undesirable ions from dialysates in tissues, among others.

No two patients receiving dialysis therapy are the same. They may differ in the degree of renal failure they are experiencing (some patients still have a small amount of residual function from their own kidneys), their metabolism and endogenous rate of generation of metabolic wastes, co-morbidities that affect metabolism and waste generation (diabetes or heart disease, for example), and even their water intake and diet (which affect metabolism and waste product generation). This is an important point, discussed further below.

Despite the fact that no two HD patients are the same, virtually all HD patients receive the same treatment-HD 'sessions' about 3× weekly for several hours per session. This 'prescription' for HD therapy was based on an analysis of patient data included in The National Cooperative Dialysis Study in the 1970s and the NIH HEMO Study, summarized by Eknoyan, et. al. (Eknoyan, G, Beck, G J, Cheung, A K, Daugirdas, J T, Greene, T, Kusek, J W, Allon, M, Bailey, J, Delmez, J A, Depner, T A, Dwyer, J T, Levey, A S, Levin, N W, Milford, E, Ornt, D B, Rocco, M V, Schulman, G, Schwab, S J, Teehan, B P, Toto, R, "Effects of dialysis dose and membrane flux in maintenance hemodialysis," New Engl Journ Med 347:2010-2019, 2002). The amount ("prescription") of dialysis treatment is based almost entirely on kinetic modeling of small solute (urea) distribution and extraction during dialysis (Depner, T A, "Approach to hemodialysis kinetic modeling," in Principles and Practice of Dialysis. 4th ed., Henrich, W L (ed.) Wolters Kluwer/Lippincott, Williams and Wilkins, Philadelphia, 2009). The success of treatment is closely monitored and adjusted accordingly (see below). During each HD session, patients are weighed (in order to assess the rate and volume of water accumulation from the dialysate into the patient), and have constant monitoring of blood pressure (blood pressure can be quite labile) and body temperature (despite warming of dialysate and patient, hypothermia is common). PD patients may be treated several times weekly, with prescription of therapy varying among individuals. The success of treatment of PD patients is generally based on serum creatinine values, metabolic state and quality of life.

Laboratory and physical examinations on each patient occur frequently. Each week (for the typical 'stable' patient), a complete blood count is performed, and each month a complete serum chemistry profile is analyzed. Each month, the urea reduction rate is calculated. Every 3-6 months, the lipid profile of each patient is assessed (dyslipidemia is a common problem in HD patients) and they are screened for the presence of hepatitis virus infections (to prevent cross-contamination of shared-use dialysis machines and as to protect dialysis center personnel from inadvertent exposure). If patients do not appear to be responding predictably to therapy or if emergent co-morbidities are changing overall clinical status, more frequent testing and adjustment of HD or PD conditions is done (Personal communication. H J Ballenger and R D Jarrett to J L Robertson, Apr. 5, 2014).

Urea, a small molecule (60 Daltons) normally generated as a byproduct of protein and amino acid metabolism, is used as a marker of small solute clearance from plasma to dialysate during HD (termed the "urea reduction rate-URR"). Since urea is a byproduct of protein metabolism, it is produced in the liver during digestion and rises and falls with consumption and processing of dietary protein and during some catabolic states. Urea is considered to be a normal product of metabolism and to be relatively non-toxic, i.e., not a significant contributor to clinical symptoms of uremia and disease progression in ESRD patients (Merrill, J P, Legrain, M, Hoigne, R, "Observations on the role of urea in uremia," Amer J Med 14:519520, 1953). Physicochemical characteristics of urea make it a suitable marker for dialysis efficacy. As a small molecule that is readily dissolved in the aqueous component of plasma, urea is readily and constantly filtered from plasma through intact nephrons in healthy kidneys. Urea is electrically neutral and crosses intact cell membranes by diffusion and facilitated transport. The movement of urea in and out of red cells is important; red cell membranes effectively transport urea and act to compartmentalize it. Other small solute molecules, such as phosphate and creatinine do not transit in red cells and this affects their distribution and clearance.

In patients with renal failure, there are insufficient intact remnant nephrons to remove urea (which is being intermittently generated by metabolism). With intermittent/constant production, but insufficient removal, urea levels in plasma ("blood urea nitrogen—BUN") rise, indicating renal dysfunction and reduced nephron mass. In a healthy person, with well-functioning kidneys and sufficient nephron mass, the value of blood urea nitrogen is 10-20 mg/dl. Values above these are suggestive of renal disease, but can be affected by state of hydration, dietary protein intake, digestion, and several other factors.

Patients with untreated ESRD commonly have BUN values >50-100 mg/dl. When a patient receives a dialysis treatment, plasma urea diffuses across the dialyzer membrane, driven by osmotic forces (low urea concentration in dialysate fluid), and is then removed as dialysate is drained and discarded. The efficiency of urea extraction is a function of type of dialyzer membrane, flow of blood and dialysate across the opposing sides of the membrane, treatment duration and frequency, and patient parameters (blood pressure, hydration (total body water and urea distribution/solute compartmentalization), state of nutrition and rate of urea generation, and residual nephron mass).

For each patient, computations of urea extraction, assessment of protein catabolism, and clinical signs indicative of proper management determine the dialysis prescription. Nephrologists adjust the prescription upwards (more frequent or intensive dialysis) if the patient is not stable or deteriorating. Most nephrologists acknowledge that while urea is useful in defining the prescription, it does not define the uremic state (or accurately reflect the many factors affecting protein metabolism).

Hemodialysis (HD) and peritoneal dialysis do not replace lost renal function. Many metabolic waste products are either too large, stereooptically-hindered, or electrostatically charged, to pass through dialyzer membranes, are bound to plasma proteins which prevent filtration, or are distributed within tissue fluid and metabolic compartments which limit exchange and equilibration with plasma. Some waste products, such as creatinine and hippurate, are partially eliminated in healthy people (with normal renal function) by secretion from cells in intact nephron segments. With the typical profound loss of intact nephrons in patients with ESRD, these secretory activities do not occur (Dobre et al., 2013). Shannon (Shannon J A, "Renal tubular excretion," Physiol Rev 19:63-93, 1939) noted, in 1939, that there may be many solutes produced and regulated by normal kidneys that we have not even identified or measured. The loss of nephron mass undoubtedly affects their clearance—but we do not know what they are or what it means to have them accumulate in ESRD patients. The loss of clearance in ESRD (and not met with HD or PD) may affect the development of uremia and clinical progression of ESRD. This is an important point, discussed further below.

Because it is fundamentally designed to remove small solute molecules, and is relatively non-selective in doing so, HD and PD may remove nutrients (vitamin C, folic acid, vitamin B12, zinc, and amino acids, for example) that are needed for physiologic functions. This non-selective loss of metabolically-important molecules may contribute to morbidity seen in most HD patients (Dobre et al., 2013; and Kopple, JD, Kalantar-Zadeh, K, "Malnutrition and intradialytic parenteral nutrition in patients with end-stage renal disease," in Principles and Practice of Dialysis. 4th ed., Henrich, WL (ed.) Wolters Kluwer/Lippincott, Williams and Wilkins, Philadelphia, 2009)). Currently, there is no routine monitoring of "desirable molecule loss" in HD.

Uremic toxins are molecules that are normally removed from the circulation by the kidney, but that accumulate in the fluids and tissues of patients with ESRD. The molecules, also referred to as uremic retention solutes, adversely affect a variety of physiologic functions, and are associated with morbidity and mortality (Duranton et al., 2012; and Meyer, T W, Hostetter, T H, "Uremia", New Engl J Med 357:1316-1325, 2007; Vanholder, R, De Smet, R, Glorieux, G, Argiles, A, Baurmeister, U, Brunet, P, Clark, W, Cohen, G, De Deyn, P P, Deppisch, R, Descamps-Latscha, B, Henle, T, J6rres A, Lemke, H D, Mass, y Z A, Passlick-Deetjen, J, Rodriguez, M, Stegmayr, B, Stenvinkel, P, Tetta, C, Wanner, C, Zidek, W; European Uremic Toxin Work Group (EUTox), "Review on uremic toxins: classification, concentration, and interindividual variability," Kidney Int. 2003 May; 63(5):1934-43, 2003). There is broad consensus that uremic toxins are not effectively removed by either form of dialysis; uremic toxins materially contribute to the perpetual illness, medical fragility, and decreased lifespan of HD patients; the type, concentration, kinetics of metabolism, and fluctuations in circulating levels of uremic toxins is highly variable among HD patients; it is not known which toxins or combinations of toxins are responsible for uremia; all toxins have not been clearly identified; and measurement of uremic toxins is not done dynamically, at the point of care, for individual patients; instead, these measurements and associated correlations are largely in the domain of research studies, done in academic centers, with sophisticated and costly analytical equipment and methodology.

There are three primary classes of uremic toxins, classified primarily on molecular mass and binding properties (with plasma components). In a comprehensive recent review of eighty-eight uremic toxins, Duranton, et. al. (Duranton et al., 2012) noted the following distribution of currently identified molecules within these classes: free water soluble, low molecular weight molecules <0.5 kD) 40/88 (46%); middle molecules, variable water solubility (0.5 kD-60 kD) 25/88 (28%); and protein-bound molecules 23/88 (25%). The methodology used to identify the 88 uremic toxins includes: ion exchange chromatography; gas chromatography and gas chromatography/mass spectroscopy; high performance liquid chromatography; spectrophotometry, nephelometry, fluorometry; chemiluminescence; radioimmunometry; and nuclear magnetic resonance spectroscopy.

The pace of discovering new uremic toxins is brisk. Comparing a comprehensive list of uremic toxins from the EUTox (European Uremic Toxin Work Group) in 2003, with an updated list from 2012, there are fifty-five new toxins on the most recent list (a 175% increase in known or suspected uremic toxins in just 8 years). Data in the most recent review/listing (Duranton et al., 2012) indicated that increased sensitivity of assay methods adjusted the concentration upward (more retention in ESRD patients on HD) for several molecules. The concentrations of some molecules (indole-3-acetic acid, free/total indoxyl sulfate, free/total p-cresyl sulfate, uric acid) were felt to be underestimated by current analytic methods, based on comparisons of multiple analytical methods and reported values.

Information presented by Duranton, et. al, (Duranton et al., 2012) showed significant variation of many molecules among individual patients (termed "high" and "low" concentration molecules). These included carboxymethyllysine, free indoxyl sulfate, and phenol-all molecules that are protein bound. Several middle molecules showed similarly high individual variation, including parathyroid hormone (PTH) fragments, TNFa, leptin, osteocalcin, and interleukin-8.

Some molecules are actually present in lower concentrations in HD patients than in patients not receiving HD. These molecules include bilirubin, reduced glutathione, a1-antitrypsin, arginine, and homoarginine. Biological functions of these molecules include vasodilation, free radical quenching/scavenging, and control of inflammation. Reduction of normal physiological concentrations of these molecules likely has some role in the morbidity associated with uremia and ESRD.

Thirty-two uremic toxins identified in the 2003 EUTox data (Vanholder, R, De Smet, R, Glorieux, G, Argiles, A, Baurmeister, U, Brunet, P, Clark, W, Cohen, G, DeDeyn, P P, Deppisch, R, Descamps-Latscha, B, Henle, T, Jörres A, Lemke, H D, Mass, y Z A, Passlick-Deetjen, J, Rodriguez, M, Stegmayr, B, Stenvinkel, P, Tetta, C, Wanner, C, Zidek, W; European Uremic Toxin Work Group (EUTox), "Review on uremic toxins: classification, concentration, and interindividual variability," Kidney Int. 2003 May; 63(5):1934-43, 2003) were found to be present at lower concentrations in patients dialyzed with current, improved methodology. This data suggests that new technologies and more aggressive HD use may significantly affect the concentrations of uremic toxins in the circulation of HD patients. From this information, it is abundantly clear that many molecules reflecting both health and disease are present in blood, plasma, urine, and, importantly, in the waste dialysis stream of hemodialysis equipment.

The present inventors have shown by analysis of dialysate waste stream samples that the composition of the dialysate waste stream changes from the beginning to the end of the dialysis cycle in terms of both the types and concentrations of dialyzable molecules present. These changes represent the kinetic efficiency of the dialysis process. Such changes are not currently and routinely monitored by any dialysis system. These important and unique observations can be used to assess the efficacy of the dialysis process and dialysis equipment.

Unless improvements are made in the process of dialysis (more efficient machines that more effectively mimic renal excretory functions, more effective application of individualized patient "prescriptions"), patients with ESRD are doomed to ongoing illness and shortened lifespans. Current laboratory methods to assess dialysis efficacy do not allow dynamic assessment of patients during and between therapies and are not designed to assess the kinetic role of uremic toxins in disease progression.

Efforts in this area and related areas include those described in U.S. Pat. Nos. 7,326,576, 8,945,936, 8,953,159, U.S. Patent Application Publication No. 20080097272, and International Publication No. WO 2012/140022. Despite these efforts, there remains a need in the art for systems and methods which improve the health assessment and management of dialysis patients.

SUMMARY OF THE INVENTION

In one embodiment, the present invention provides a system and method for monitoring, through Raman spectrometry in real-time and at the point of patient care, the efficiency of dialysis or transplant allograft function in removing toxic metabolic wastes and other target analytes from patients with End Stage Renal Disease (ESRD). Embodiments of the system and method of the invention capture a 'molecular footprint' of Raman spectra that indicate the presence or concentration of one or more target analytes during dialysis sessions and dynamically analyze their removal from blood. This also includes similar measurements in urine from dialysis or renal transplant patients. Through the use of algorithms, the Raman spectra of one or more target analytes may be compared to those stored in memory, and one or more dialysis treatment outcome characteristics may be determined. In addition, the system and method may be used to determine unique metabolic waste signatures for individual patients and provide a means for longitudinal assessment of dialysis efficiency during individual or chronologically separate dialysis treatments, and from these assessments treatment decisions may be made. Further, effects of intercurrent disease morbidities on the production of toxic metabolic wastes can be assessed with the system and method of the present invention, further improving individual patient care. Embodiments of the system of the invention can be economically retrofitted to existing hemodialysis systems as well and used effectively in multipatient hemodialysis centers. As well, embodiments of the system of the invention can be applied to the analysis of urine or other fluids from patients being treated for renal failure.

BRIEF DESCRIPTION OF THE DRAWINGS

The accompanying drawings illustrate certain aspects of embodiments of the present invention, and should not be used to limit the invention. Together with the written description the drawings serve to explain certain principles of the invention.

FIG. 5 is a table showing characteristics of six hemodialysis patients and samples associated with them that were the subject of Raman analysis of dialysate.

DETAILED DESCRIPTION OF VARIOUS EMBODIMENTS OF THE INVENTION

Figure 1:
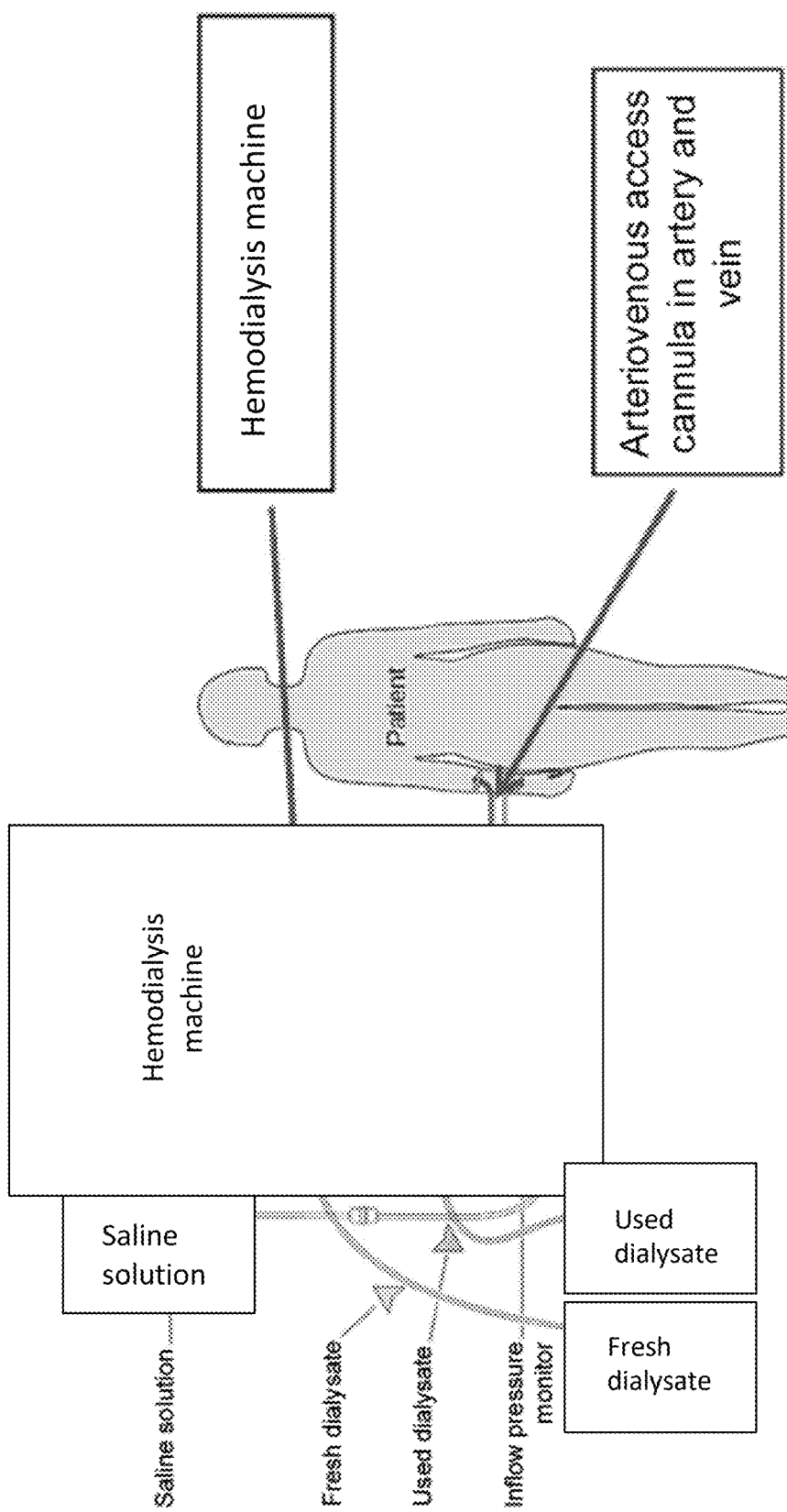
FIG. 1 is a schematic diagram of a conventional hemodialysis system.

Reference will now be made in detail to various exemplary embodiments of the invention. It is to be understood that the following discussion of exemplary embodiments is not intended as a limitation on the invention. Rather, the following discussion is provided to give the reader a more detailed understanding of certain aspects and features of the invention.

Raman spectroscopy is a spectroscopic technique based on inelastic scattering of monochromatic light (termed the "Raman effect"). This occurs when a photon of monochromatic light interacts with a molecule to be measured (sample), resulting in absorption and reemission (scattering) at a different frequency than the monochromatic light. Different functional groups produce characteristic peaks in a plot of intensity versus Raman shift. In this way, the chemical composition of a sample may yield a molecular "fingerprint" which can be analyzed. Raman spectroscopy is particularly advantageous in that it can be used on a variety of samples with little or no sample preparation, and requires small sample volumes (e.g. 1 µl).

The present inventors have determined that several Raman spectroscopic methods can be used to acquire meaningful signatures of chemical composition of analytes in biological fluids and other samples. When the analytical data from these spectroscopic measurements are computationally normalized and then processed and further analyzed, the resultant data produces biologically relevant information that can be used to determine states of health and disease.

Embodiments of the present invention provide methods and systems based on applied methods of Raman spectroscopy that will allow a clinician to analyze the molecular components in fluid samples and to utilize the analysis of these components to assess health and disease, and in particular, the health of dialysis and transplant patients. In embodiments, the system provides objective quantitative data that, when combined with disease-specific logical algorithms, can be used to modify disease treatments and which can assist in the development of individual patient-specific medical therapy.

Provided by embodiments of the invention is a method for determining dialysis treatment efficacy, the method comprising: providing a Raman spectrum of analytes present in a patient sample associated with a dialysis patient; providing one or more Raman spectrum of analytes present in one or more reference sample associated with the dialysis patient and/or associated with other dialysis patients; comparing the Raman spectrum of the dialysis patient with the one or more reference samples to determine whether an analyte pattern of two or more select analytes is present in both; and based on the comparing, determining disease state status of the patient. Similarly, embodiments can be used to determine functioning of renal transplants by analysis of urine specimens from transplant patients.

According to methods of the invention, the analyte pattern can comprise two or more analytes chosen from creatinine, uric acid, uric acid based compounds, interleukin-8, bilirubin, a1-anti-trypsin, arginine, homoarginine, urea, urea-based compounds, urea nitrogen based compounds, ammonium-based compounds, nitrogen-based compounds, vitamins, vitamin C, vitamin B12, folic acid, zinc, amino acids, proteins, nucleic acids, pharmaceutical compounds, 2-heptanal, 2-hexenal, 2-nonenal, 4-decenal, 4-HO-decenal, 4-HO-hexenal, 4-HO-nonenal, 4-HO-octenal, 4 pyrididone-3-carboxy-1-β-D-ribonucleoside, 8-Hydroxy-2'deoxyguanosine, α Keto δ guanidinovlaeric acid, antranilic acid, argininic acid, asymmetric and symmetric dimethylarginine, cysteine, decanal, dimethylamine, ethylamine, guanidine, guanidinoacetic acid, guanidine succinic acid, hepatanal, hexanal, hypoxanthine, malondialdehyde, methylguanidine, monomethylamine, neopterine, nicotinamide, N methyl-2-pyridone-5-carboxamide, N-methyl-4-pyridone-3-carboxamide, nonanal, noradrenaline, oxalate, phenylacetic acid, dimethylarginine, trimethylamine, trimethylamine-N-oxide, 3 carboxy-4-methyl-5-propyl-2-furan-propanoic acid, acrolein, carboxymethyllysine, dihydroxyphenylalanine, hippuric acid, homocysteine, indicant, indole-3-acetic acid, indoxyl sulfate, indoxyl-β-D-glucoronide, kynurenic acid, p-cresyl sulfate, pentosidine, phenol, putrescine, permidine, thiocyanate, α1-acid glycoprotein, α1-microglobulin, β-trace protein, 32 microglobulin, adiponectin, angiogenin, calcitonin, complement factor D, cystatin C, fibroblast growth factor-23, glutathione, reduced glutathione, IGF-1, IL-6, IL-8, IL-10, leptin, hemoglobin, myoglobin, osteocalcin, parathyroid hormone (PTH), prolactin, resistin, retinal binding protein, soluble intracellular adhesion molecule-1, TNF-α, and vascular endothelial growth factor. The number of analytes selected for the fingerprint pattern is not critical and can range from 2 to 1,000, such as from 5-500, or from 10-300, or from 15-200, or from 25-100, or any range in between. Any one or more of the analytes mentioned in this specification can be used, and in any combination, even with other analytes.

Methods of embodiments of the invention can further comprise determining if there are any differences between the analyte patterns of the Raman spectrum of the reference and patient samples. Such analysis is helpful for determining the extent of a disease state of a patient, especially to determine if a patient's health is improving or deteriorating in response to hemodialysis treatment.

According to such methods, the one or more reference sample is typically collected at a time previous to collection of the patient sample. The reference sample can also be collected after the treatment, if associated with other dialysis or transplant patients that are not the subject dialysis or transplant patient. In embodiments, the one or more reference sample is associated with the dialysis or transplant patient, and/or associated with other dialysis or transplant patients.

The patient sample of such methods is preferably a dialysate, blood, or plasma, or urine, but can be any sample from or associated with a patient.

In one embodiment, the present invention provides a method for monitoring target analytes in one or more biological fluids of interest. The methods include irradiating the biological fluid of interest with light to produce one or more spectrum and detecting the spectrum with a detector. The biological fluids of interest are preferably those related to dialysis, including hemodialysis and peritoneal dialysis. For example, the biological fluids of interest irradiated with light may include blood entering a hemodialysis system, blood exiting a hemodialysis system, used dialysate exiting a dialysis system, or urine. In a preferred embodiment, the fluids are irradiated with monochromatic light, and one or more Raman spectra are detected as a result of the irradiation. The fluids may be irradiated within the dialysis tubing itself, or removed from the dialysis tubing and irradiated in a separate chamber.

The one or more Raman spectra may represent one or more target analytes that are indicative of the health of a dialysis or transplant patient. Thus, one embodiment of the invention comprises the steps of a) irradiating a sample representing a biological fluid of interest, wherein the biological fluid of interest relates to a dialysis or transplant patient b) detecting one or more Raman spectra of one or more target analytes from the sample and c) determining the health of the dialysis or transplant patient based on the Raman spectra of the one or more target analytes. In this embodiment, the health of the dialysis or transplant patient may include any observation that is associated with dialysis or transplantation of ESRD patients, including an assessment of uremia, an observation of uremic toxicity, an observation of loss of vital nutrients, an observation of altered pharmacokinetics of a pharmaceutical being administered to a patient, the presence or risk for complications associated with dialysis, transplantation, or end-stage renal failure, and the like. The one or more target analytes may include combinations of analytes that provide characteristic signatures of the above.

In another embodiment, the one or more Raman spectra may represent one or more target analytes that are used to monitor the efficacy of a dialysis treatment. Thus, one embodiment of the invention comprises the steps of a) irradiating a sample representing a biological fluid of interest, wherein the biological fluid of interest relates to a dialysis patient, b) detecting one or more Raman spectra of one or more target analytes from the sample, and c) monitoring the efficacy of the dialysis treatment based on the Raman spectra of the one or more target analytes. In this embodiment, the efficacy of dialysis treatment may be monitored by following the change in concentration, or kinetics, of one or more target analytes over time. The one or more target analytes may include urea or other related nitrogenous compounds, or may be distinct from and unrelated to urea. The target analytes may include combinations of analytes that provide characteristic signatures on the progress of dialysis treatment.

In an additional embodiment, the method above may further include: d) making a dialysis treatment decision based on the monitoring of the efficacy of the dialysis treatment. The dialysis treatment decision may include 1) increasing or decreasing the amount of time that the patient is on the dialyzer, 2) increasing or decreasing the blood flow through the dialyzer, or 3) a combination of these.

In embodiments of the methods of the invention, either the presence or the concentration of the one or more target analytes may be monitored. The one or more target analytes may be compared to one or more reference analytes. For example, the presence or concentration of one or more target analytes may be followed in a single patient and compared to one or more reference values. The one or more reference values may be indicative of a clinical observation associated with dialysis treatment. For example, in one embodiment, when one or more target analytes exceed concentrations stored in memory, a finding of uremic toxicity may be inferred.

Additionally, the presence or concentration of one or more target analytes in a single patient may be compared to those measured in the fluids of other dialysis or transplant patients or groups of dialysis or transplant patients. The other patients or groups of patients may have common clinical characteristics related to end-stage renal failure, dialysis, or transplantation, including efficacy or complications of treatment, and these may be indicated by characteristic signatures of Raman spectra. In this way, Raman spectra from an individual patient may be compared to those representing a clinical observation associated with dialysis or transplantation treatment, and from this, clinical observations may be inferred from the Raman spectra of the patient.

In another embodiment, the present invention provides a method for monitoring dialysis of a patient. The method may comprise a) irradiating a sample of blood or dialysate from a dialysis patient, b) obtaining Raman spectra of one or more target analytes, c) comparing the obtained spectrum to one or more Raman spectra stored in memory, and d) analyzing or comparing the obtained Raman spectra with those stored in memory to determine a dialysis treatment characteristic of a patient. The blood or dialysate can be irradiated with a probe that is configured to emit monochromatic light and receive Raman scattered light. The probe can be configured to irradiate a sample in a dialysis tube of a patient in real-time or near real-time to determine the presence and/or concentration of an analyte in the dialysis tube. Alternatively the sample may be separated from the flow of dialysis fluid or may be a urine specimen or other biologically-derived fluid for carrying out the determination of the presence and/or concentration of the analytes.

Figure 2:
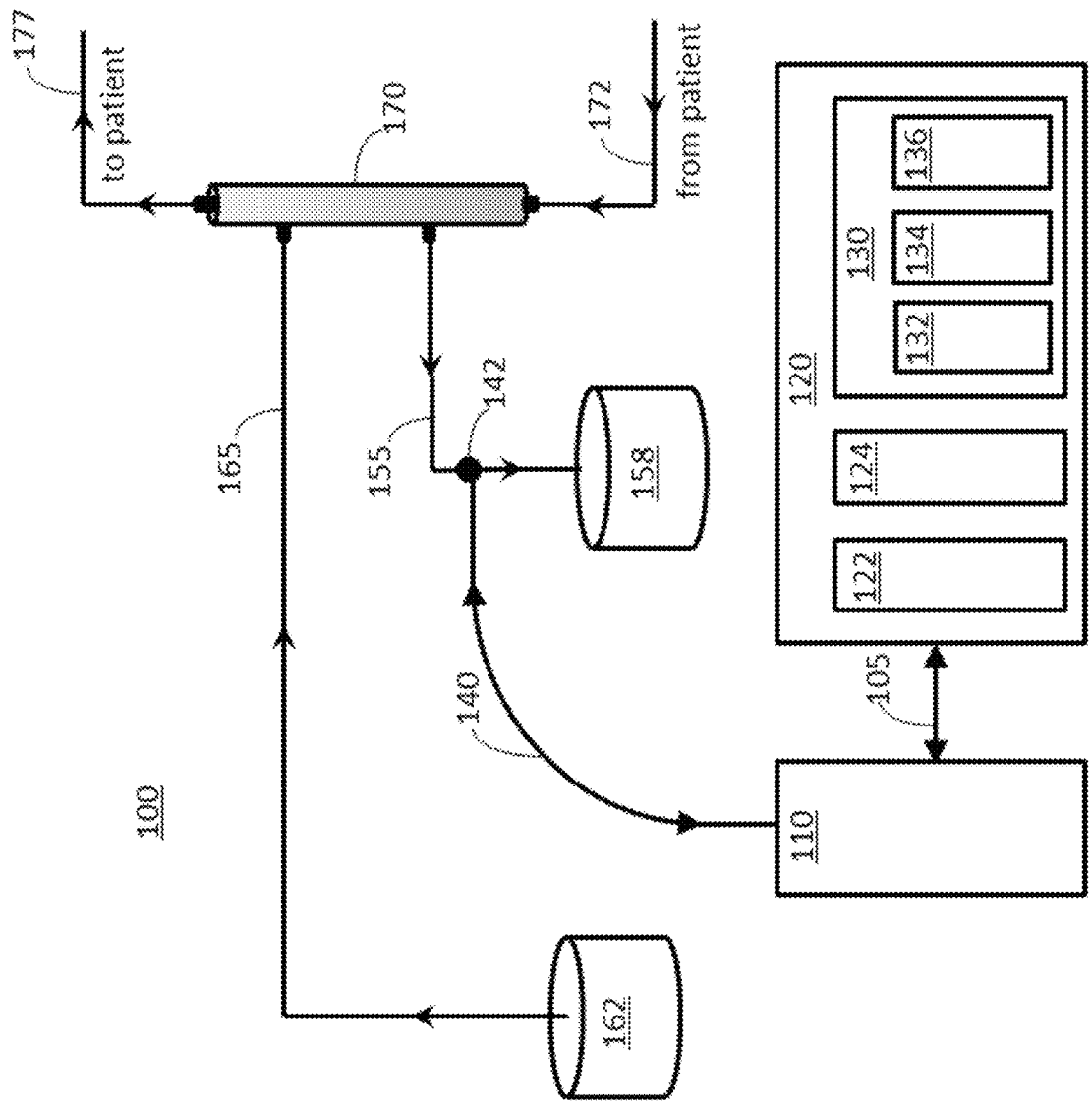
FIG. 2 is a schematic diagram of an embodiment of a system according to the invention.

In another embodiment, shown in FIG. 2, the present invention provides a system 100 comprising a Raman spectrometer 110 operably connected to a computing device 120, through a cable 105 (or wireless connection, not shown). The computing device 120 comprises an input/output device 122 and one or more processors 124 operably connected to a memory 130. The memory can comprise a set of computer-executable instructions 132 for performing the algorithms of the invention and one or more databases 134, 136 for storing spectra obtained from the Raman spectrometer. The databases 134, 136 may include patient-specific, group-specific, and/or dialysis treatment outcome-specific Raman spectral signatures. In embodiments, the Raman spectrometer 110 may comprise an excitation source, a sampling apparatus, and a detector. In one embodiment, the excitation source is a laser, the detector is a spectrometer, and the sampling apparatus is a fiber optic probe 140 that terminates in chamber 142 connected to the dialysate waste output tube 155 coming from dialyzer 170, which tube ends in waste dialysate collection container 158. Dialyzer 170 has fresh dialysate intake 165 originating from fresh dialysate container 162. Dialyzer 170 also has removed blood input 172 originating from a patient (not shown) and clean blood output 177 returning to the patient.

The Raman spectrometer may be a benchtop or a handheld spectrometer. Examples of benchtop Raman spectrometers include those described in U.S. Pat. Nos. 5,786,893; 5,534,997; and 6,100,975. Examples of handheld Raman spectrometers are described in U.S. Pat. Nos. 7,505,128; 7,524,671; 7,651,851 and 8,699,020, and U.S. Patent Application Publication No. 20140052386 A1. The fiber optic probe may have a dichroic mirror, which separates Raman scattered light from laser light by reflecting laser light and allowing Raman-scattered wavelengths to pass. Laser light and Raman scattered light may be transmitted through separate fibers (collection fiber(s) and excitation fiber(s)). Filters may be placed before the fibers for blocking undesirable wavelengths, such as a long pass filter placed before the collection fiber (blocks reflected laser light) and a band-pass filter placed before the excitation fiber (blocks Raman scattered light). The fiber optic probe may include one or more lenses for focusing the light onto the sample or onto the fibers. An example of such a fiber optic probe is the RAMANPROBE™, described in U.S. Pat. No. 5,112,127. Another example is a Raman fiber optic probe embedded in a microfluidic device, described in U.S. Pat. No. 8,638,431. Another example is a dual and multi-wavelength Raman sampling probe described in U.S. Patent Application Publication No. 20120099102.

The laser may emit monochromatic light at any wavelength, including far infrared, mid infrared, infrared, near infrared, visible light, ultra-violet, and extreme-ultraviolet, or at multiple wavelengths. The choice of wavelength may depend on the target molecule one wishes to measure. For example, for visible wavelengths such as blue or green can be good for inorganic molecules, while ultraviolet wavelengths may be optimal for measuring biomolecules such as proteins, RNA, and DNA as these tend to absorb UV radiation. In addition, embodiments may include multiple lasers to represent multiple wavelengths.

The Raman spectra stored in memory may be those from the same patient, and/or those from different patients. In one embodiment, the Raman spectra stored in memory are obtained from one or more earlier samples during the course of dialysis. By comparing the Raman spectra from a current sample to that of one or more previous samples, the time course of dialysis may be monitored. Through this way, the kinetics of one or more target analytes may be followed, either in the blood or the waste dialysate of the patient, and the progress of the dialysis may be monitored as well as potential complications. The target analytes may include one or more uremic toxins, nutritional factors, electrolytes, and pharmaceutical compounds or metabolites. The target analytes may include urea or related compounds, or may be unrelated to urea.

In another embodiment, the Raman spectra stored in memory may be those from different patients. For example, the Raman spectra stored in memory may be from one or more groups of patients, wherein each group shares one or more dialysis treatment characteristics. In this embodiment, Raman spectra obtained from the patient can be compared with those representative or not representative of a dialysis treatment characteristic using an algorithm which classifies the patient's spectra according to how much it resembles the spectra of the two groups. In this way, the patient may be assigned a dialysis treatment characteristic based on the classification. The dialysis treatment characteristic may include successful treatment, failed treatment, incomplete treatment, or complicated treatment.

In embodiments, the Raman spectra provide characteristic signatures that are indicative of one or more dialysis treatment characteristics. The Raman spectra may represent a single analyte or multiple target analytes, including anywhere from 2 to 100 analytes or more. The characteristic signatures may indicate a variety of treatment outcomes. For example, one group of Raman spectra may be highly indicative of uremic toxicity, while another group of Raman spectra may be highly indicative of a nutritional deficiency resulting from the dialysis procedure. Another group of Raman spectra may be indicative of altered pharmacokinetics of a pharmaceutical resulting from the dialysis procedure. Another group of Raman spectra may indicate complications of either the dialysis procedure itself or end-stage renal disease. The groups of Raman spectra may be generally composed of the spectra of 2-10 analytes, but larger groups are possible.

Thus, one embodiment of the invention provides a method comprising a) providing a plurality of Raman spectra representative of one or more target analytes stored in memory, b) receiving spectra from a Raman spectrometer of the one or more target analytes obtained from a sample from a dialysis patient, and c) analyzing the received spectra with a processor; wherein the analysis is based on the plurality of spectra stored in memory and provides an indication of a dialysis treatment characteristic of the patient.

In one aspect of this embodiment the plurality of Raman spectra are obtained from samples from at least a first and second group of patients having different dialysis treatment characteristics and an algorithm is used to classify the dialysis treatment characteristic of the patient based on the plurality of Raman spectra of the first or the second group of patients.

In another aspect of this embodiment, the plurality of Raman spectra representative of one or more target analytes stored in memory are obtained from a sample of the patient at a first time point, the spectra is received at second later time point, and the spectra from the second time point is compared to the spectra of the first time point to provide an indication of the dialysis treatment characteristic of the patient Another embodiment comprises a method for monitoring the health of dialysis patients, the method comprising a) receiving spectra from a Raman spectrometer of one or more target analytes obtained from a first sample from a dialysis patient at a first time point, b) storing the spectra in memory, c) receiving spectra from a Raman spectrometer of one or more target analytes obtained from a second sample from the dialysis patient at a second later time point, d) comparing the Raman spectra from the second time point with the Raman spectra from the first time point with a processor, and e) determining a dialysis treatment outcome characteristic of the dialysis patient based on the comparison.

The one or more target analytes can be urea or related molecules. In other embodiments, the target analytes are not related to urea. The one or more target analytes may be selected from the group comprising, consisting of, or consisting essentially of uremic toxins, nutritional factors, electrolytes, and pharmaceutical compounds (such as acetaminophen or acetylsalicylic acid) or metabolites.

The dialysis treatment characteristic may be selected from the group comprising, consisting of, or consisting essentially of successful treatment, failed treatment, and complicated treatment. Further, the dialysis treatment outcome characteristic may be based on the kinetics of the one or more target analytes. In embodiments, the method may further comprise making a treatment decision based on the dialysis treatment characteristic. For example, the treatment decision may determine whether to continue or terminate dialysis treatment.

Another embodiment comprises a method for monitoring the health of dialysis patients, the method comprising a) providing one or more reference sets of a plurality of Raman spectra of one or more target analytes stored in memory, wherein the reference sets represent one or more dialysis treatment outcome characteristics, b) receiving spectra from a Raman spectrometer of the one or more target analytes obtained from a sample from a dialysis patient, c) analyzing the received Raman spectra with a processor according to an algorithm, wherein the analysis is based on a comparison of the received Raman spectra with the plurality of Raman spectra stored in memory, and d) determining a dialysis treatment outcome characteristic of the dialysis patient based on the analysis.

Another embodiment provides a method comprising a) providing a plurality of Raman spectra representative of one or more target analytes stored in memory wherein the plurality of Raman spectra are obtained from samples from at least a first and second group of dialysis patients, wherein the first group of patients share a first dialysis treatment outcome characteristic and the second group of patients share a second dialysis treatment outcome characteristic, b) receiving spectra from a Raman spectrometer of the one or more target analytes obtained from a sample from a dialysis patient, c) analyzing the received spectra with a processor according to an algorithm, wherein the analysis is based on the plurality of spectra stored in memory and is used to classify the patient's treatment outcome characteristic according to the first or the second group of patients.

In one aspect of these embodiments, the first dialysis treatment outcome characteristic is the presence of uremia and the second treatment outcome characteristic is the absence of uremia.

In another aspect of these embodiments, the first dialysis treatment outcome characteristic is the presence of one or more uremic toxins above a concentration threshold and the second dialysis treatment outcome characteristic is the absence of one or more uremic toxins above the concentration threshold.

In another aspect of these embodiments, the first dialysis treatment outcome characteristic is the presence of one or more nutritional factors above a concentration threshold and the second dialysis treatment outcome characteristic is the absence of one or more nutritional factors above the concentration threshold.

In another aspect of these embodiments, the first dialysis treatment outcome characteristic is the presence of one or more complications from end-stage renal failure and the second dialysis treatment outcome characteristic is the absence of one or more complications of end-stage renal failure.

In another aspect of these embodiments, the first dialysis treatment outcome characteristic is the presence of one or more dialysis complications and the second dialysis treatment outcome characteristic is the absence of one or more dialysis complications.

In another aspect of these embodiments, the first dialysis treatment outcome characteristic is successful treatment and the second dialysis treatment outcome characteristic is treatment failure.

In the methods of the invention, the analytes (or "target analytes" used interchangeably herein) can be measured in various fluid lines of a kidney hemodialysis machine or from a peritoneal catheter in the case of peritoneal dialysis. Kidney dialysis machines are well known in the art and are illustrated, for example, in U.S. Pat. Nos. 3,598,727, 4,172,033, 4,267,040, and 4,769,134 6,284,131. In one embodiment, the analytes are measured in the used dialysate (dialysate exiting the dialyzer). In another embodiment, the analytes are measured in blood entering the hemodialysis machine (from the patient). In another embodiment, the analytes are measured in the blood exiting the hemodialysis machine (to the patient). Used dialysate will typically contain target analytes (e.g. waste products) extracted from blood entering the dialyzer. The other constituents of used dialysate are excess electrolytes leaving the dialyzer. However, used dialysate should provide a cleaner sample as it is absent Raman spectra from blood constituents. As used herein a "sample from a dialysis patient" includes direct samples (e.g. blood leaving the dialysis patient) as well as indirect samples (e.g. blood exiting the dialysis machine or waste dialysate).

The analytes can be measured in the tubing entering or exiting the hemodialysis machine. For example, in one embodiment, a laser beam can be directed into a segment of the dialysis tubing (used in either hemodialysis or peritoneal dialysis). In another embodiment, a probe such as a miniaturized fiber optic probe can be inserted into the dialysis tubing. In another embodiment, surface enhanced Raman spectroscopy (SERS) sensors, such as those described in U.S. Pat. No. 8,953,159, are placed in the dialysis tubing. Alternatively or in addition, one or more of the analytes can be measured in samples taken from the patient, including blood, plasma, urine, feces, saliva, and cerebrospinal fluid.

In one embodiment, the analytes are intermediates or end-products of metabolic processes occurring in the patient. The intermediates or end-products may be a result of anabolism, catabolismenergy transformations, xenobiotic transformations, microbial reactions, among others. The intermediates or end-products may be freely soluble in blood, or bound to proteins specifically or non-specifically, and may be organic or inorganic molecules, and/or found in urine. In another embodiment, the analytes are biomolecules such as proteins or nucleic acids. Examples of protein analytes include antibodies or antibody fragments, structural proteins, enzymes, messenger proteins, and transport/storage proteins. Non-limiting examples of nucleic acids analytes include genomic DNA, mRNA, rRNA, tRNA, siRNA, and ribozymes. Additionally, the analytes may be indicators of the nutritional status of the patient (e.g. vitamins, minerals, cofactors). In an exemplary embodiment, the analytes, as described herein, are uremic toxins, or suspected uremic toxins. The uremic toxins, or suspected uremic toxins, may have (or may be suspected to have) deleterious effects on a dialysis patient as a result of a shift in blood concentration in comparison to levels that occur in the population with normal renal function. The uremic toxins may have deleterious effects through a variety of mechanisms, such as by inhibiting enzymes, transport functions, protein synthesis, DNA synthesis, energy transformations, metabolism, and the like. Alternatively or in addition, one or more of the analytes may include one or more xenobiotics (e.g. pharmaceutical compounds).

In embodiments, analytes that can be measured according to the methods of the invention include, but are not limited to, free water-soluble low molecular weight molecules, protein-bound molecules, and mid-range molecular weight molecules. Examples of free water-soluble low molecular weight molecules that can be measured according to methods of the invention include, without limitation 2-heptanal, 2-hexenal, 2-nonenal, 4-decenal, 4-HO-decenal, 4-HO-hexenal, 4-HO-nonenal, 4-HO-octenal, 4-pyridinone-3-carboxy-1-β-D-ribonucleoside, 8-Hydroxy-2'deoxyguanosine, α-Keto-δ-guanidinovlaeric acid, antranilic acid, argininic acid, asymmetric dimethylarginine, cysteine, decanal, dimethylamine, ethylamine, guanidine, guanidinoacetic acid, guanidine succinic acid, hepatanal, hexanal, hypoxanthine, malondialdehyde, methylguanidine, monomethylamine, neopterine, nicotinamide, N-methyl-2-pyridone-5-carboxamide, N-methyl-4-pyridone-3-carboxamide, nonanal, noradrenaline, oxalate, phenylacetic acid, symmetric dimethylarginine, trimethylamine, trimethylamine-N-oxide, and uric acid. Examples of protein-bound molecules that can be measured according to methods of the invention include, without limitation 3-carboxy-4-methyl-5-propyl-2-furanpropanoic acid, acrolein, carboxymethyllysine, dihydroxyphenylalanine, hippuric acid, homocysteine, indicant, indole-3-acetic acid, indoxyl sulfate, indoxyl-β-D-glucoronide, kynurenic acid, p-cresyl sulfate, pentosidine, phenol, putrescine, permidine, and thiocyanate. Examples of midrange molecular weight molecules that can be measured according to methods of the invention include, without limitation, α1-acid glycoprotein, α1-microglobulin, β-trace protein, β2-microglobulin, adiponectin, angiogenin, calcitonin, complement factor D, cystatin C, fibroblast growth factor-23, glutathione, oxidized glutathione, IGF-1, IL-6, IL-8, IL-10, leptin, hemoglobin, myoglobin, osteocalcin, PTH, prolactin, resistin, retinal binding protein, soluble intracellular adhesion molecule-1, TNF-α, and vascular endothelial growth factor. Additionally, the analytes may include any molecule listed in the EUTox Uremic Toxin Database (maintained by the EUTox Work Group, a working group of the "European Society of Artificial Organs" (ESAO) and an endorsed working group of the "European Renal Association-European Dialysis Transplantation Association" (ERA-EDTA)). The analytes may include any molecule recited above, or any combination of molecules recited above.

In some cases, the target analytes may indicate pathological processes in a dialysis patient, such as a necrotic process (e.g. liver enzymes) or an inflammatory process (cytokines). Additionally, the target analytes may be factors that are prognostic or diagnostic of other pathological processes (cancer, heart disease). By measuring these target analytes in the blood, urine, or dialysate of a patient, the health of the patient may be inferred.

The presence and/or the concentration of the analytes may be determined. The analytes may be measured either as raw spectral intensity measurements or normalized measurements, or converted to concentration values. For example, U.S. Pat. No. 7,326,576 discloses the ability of Raman spectroscopy to produce a concentration correlation with intensity values for urea measured in human blood plasma samples to which increasing amounts of urea were added. The results showed a linear correlation between the peak height at 1001 cm$^{-1}$ and urea concentration. In embodiments of this invention, however, this invention does not limit its analysis to urea, and includes other target analytes including combinations or groups of analytes which may be more clinically significant measures of uremic toxicity than urea itself. As provided above, urea itself is relatively non-toxic and does not contribute significantly to the symptoms of uremia. However, it is conceivable that the concentrations of other analytes could be determined in a similar manner, not just limited to blood but other medical fluids of interest such as dialysate, urine, feces, etc. In embodiments, Raman-based CHEMOMETRIC FINGERPRINTING™ can be performed, where a fingerprint or pattern of a number of select analytes is compared between the test sample (patient sample) and the reference data to determine health of a patient and/or efficacy of treatment.

In one embodiment, the analytes are selected to provide a measurement of toxicity to the patient. In one embodiment, the analytes include urea-based compounds, urea nitrogen based compounds, ammonium-based compounds, uric acid based compounds, and nitrogen-based compounds. Hence, in one embodiment, the methods of present invention are directed to monitoring the levels of blood urea nitrogen in patients undergoing dialysis. However, in other embodiments, the analytes include molecules or a combination of molecules that don't reflect the level of blood urea nitrogen, but provide a better indication of uremic toxicity. Thus, in some embodiments, the analyte or analytes are not urea or not chemically related to urea.

The term "level" or "levels" of an analyte, as used herein, refers to concentration of a constituent, such as a constituent of a dialysate fluid. The concentration levels are readily derivable from Raman spectral measurements. Thus, the "level" can also be measured based on Raman spectral data. Without the need, in all instances, to convert such data into concentration values. The term "level" is also meant to include the magnitude of a quantity considered in relation to an arbitrary reference value. For example, a look-up table can be used for plotting predictions of analyte concentration versus a reference comprising of healthy individuals or threshold concentrations in healthy individuals. In other embodiments, a standard curve generated from known analyte concentrations can be used.

In carrying out embodiments of methods of the invention, several commercially-available Raman spectroscopic devices can be used for initial data acquisition from samples, and a number of other devices that are commercially-available can be used to increase the convenience and accuracy of the Raman spectroscopic analytical data. These devices are manufactured by various commercial ventures and are readily available.

In embodiments of the method, fluids generated during human patient hemodialysis or peritoneal dialysis, specifically the dialysate waste stream, contain dialyzable molecules that can be collected during the dialysis process and analyzed with Raman spectroscopic methods. Patient urine specimens may also be collected and analyzed by these methods. Once raw data acquisition has taken place, the raw spectroscopic information can be subjected to computational normalization and then to complex computational analysis through one or more algorithms. The algorithms may be any one of machine learning or predictive or classification algorithms such as hierarchical clustering, k-means clustering, linear discriminant analysis, principle components analysis, logistic regression, support vector machines, k-nearest neighbor, decision trees, neural networks, Bayesian networks, and Hidden Markov models.

The analysis of specific molecules in the waste dialysate, urine, or other fluids, derived from computations of the invention can be used to determine observations relevant to the management of kidney failure with dialysis or after transplantation. This includes evaluation of the health of dialysis patients, evaluation of the efficacy of the dialysis treatment, and longitudinal health monitoring. These observations may relate to diagnostic or prognostic biomarkers of complications of end stage renal disease or complications of the dialysis treatment itself. The diagnostic or prognostic biomarkers may be population-specific, race-specific, age-specific, gender-specific, or patient-specific. The diagnostic or prognostic biomarkers may indicate or predict one or more complications of end-stage renal disease, including anemia, bleeding from the stomach or intestines, bone, joint, and muscle pain, changes in blood sugar (glucose), nerve damage, fluid buildup around the lungs, high blood pressure, heart attack, and heart failure, high potassium levels, increased risk of infection, liver damage or failure, malnutrition, miscarriages or infertility, restless legs syndrome, stroke, dialysis dysequilibrium syndrome, seizures, and dementia, swelling and edema, and weakening of the bones and fractures. Conversely, the analytes may be prognostic of favorable treatment outcomes of dialysis where these complications are prevented or delayed.

The system and method of the invention are useful for a variety of applications related to ongoing monitoring and the management of health of dialysis and renal transplant patients. In one application, the urea reduction efficiency for a patient undergoing dialysis can be determined in real-time or near real-time and a kinetic plot of dialysis efficiency can be generated based on the urea reduction rate kinetics. Efficiency may be determined by one of two parameters. Urea reduction ratio (URR) indicates the reduction in urea as a result of dialysis and is commonly expressed as a percentage. Kt/V is another indicator of dialysis adequacy, where K stands for the dialyzer clearance, the rate at which blood passes through the dialyzer, expressed in milliliters per minute (mL/min), t stands for time, Kt, is clearance multiplied by time, representing the volume of fluid completely cleared of urea during a single treatment, and V is the volume of water a patient's body contains. The Kt/V is mathematically related to the URR and is in fact derived from it, except that the Kt/V also takes into account two additional factors 1) urea generated by the body during dialysis 2) extra urea removed during dialysis along with excess fluid. A patient's URR or Kt/V can be increased either by increasing time on dialysis or increasing blood flow through the dialyzer.

In another application, the chemical composition of the dialysate waste stream can be determined in real-time or near real-time, which can be used to determine the clearance of many medically important molecules during the process of dialysis. The medically important molecules may be any of the analytes described above. The analytes may be used as indicators of dialysis efficiency or as indicators or predictors of complications of failed dialysis or end-stage renal failure or as indicators or predictors of successful dialysis treatment.

In another application, the presence and amount of certain molecules that are by-products of metabolism, termed "uremic toxins" or "suspected uremic toxins" as discussed previously, can be determined in real-time or near real-time, and these can be partially or fully acquired through dialysis and which may be present in the dialysate waste stream or the patient's blood. These may be used as indicators or predictors of complications of inadequate dialysis treatment.

In another application, the efficiency and accuracy of each individual dialysis treatment for each patient can be determined, and this information can be stored, compared, and used on an ongoing temporal basis to determine adequacy or limitations of therapy. These stored measurements can be subsequently used to revise and plan dialysis therapy specific for each patient and which could be adjusted to changes in the health and well-being of the patient.

In another application, comparison of samples from individuals, between individuals, and among groups of individuals undergoing dialysis treatment, the presence or persistence of novel molecules that may indicate changes in the patterns of disease, including insights into etiologies, comorbidities, and progression to treatment failure, can be ascertained.

In another application, by application of these tools and methods, advantages and disadvantages associated with specific components of hemodialysis machines, including dialyzer coils and dialyzer coil membranes, can be gauged.

In another application, by application of these tools and methods, advantages and disadvantages associated with the frequency and type of hemodialysis can be obtained, including benefits and risks of the use of high- and low-flux dialyzer membranes, and more/less frequent use of dialysis (number of treatments per week, duration of individual treatments, intervals between treatments), In another application, the need for nutritional and metabolic supplementation for individual patients to replace or maintain biologically-important molecules such as vitamins, minerals, and amino acids, that may be unintentionally lost during the process of dialysis, may be ascertained. This can be based on the presence of these nutrients in fluids such as dialysate, blood, and urine. From these values, the degree and kinetics of loss during the process of dialysis can be obtained.

In another application, modifications that can be made to the composition of the dialysate fluid can be determined, making it more efficient for the dialysis process and improving the temporal health outcomes for the patient. The modifications can be made based on the efficiency of the dialysis determined from methods of the invention.

In another application, the need for changing (increasing/decreasing) the dosages of pharmaceuticals used to manage patient disease that may be unintentionally lost during the process of dialysis can be determined. This can be based on the presence of the parent compound or metabolites in fluids such as dialysate, blood, and urine. From these values, the degree and kinetics of loss during the process of dialysis can be obtained.

In another application, molecules that are markers of disease that may be then used as the basis for improved medical management with pharmaceuticals can be ascertained.

In another application, the viability of renal transplants can be evaluated. Blood and urine samples can be measured to determine renal clearances of urea or alternative markers of renal sufficiency.

In another application, the system and method of the invention can be used for drug metabolism/kinetics studies. These studies can be performed on end-stage renal failure patients (including those receiving and not receiving dialysis) as well as patients with normal renal function.

A method of determining a patient-specific dialysis prescription is also included in embodiments of the invention, the method comprising: subjecting a patient to a dialysis treatment based on a first dialysis prescription; during the dialysis treatment, taking multiple samples associated with the patient; measuring a Raman spectrum of analytes present in the samples; determining the kinetics of the analytes based on the Raman spectrum; and modifying the first dialysis prescription based on the kinetics of the analytes to produce a second dialysis prescription that is patient-specific. According to such methods the samples can be taken at various time interval, such as at the beginning, middle, and end of the dialysis treatment.

The analytes monitored according to such methods can be chosen from one or more of creatinine, uric acid, uric acid based compounds, interleukin-8, bilirubin, α1-anti-trypsin, arginine, homoarginine, urea, urea-based compounds, urea nitrogen based compounds, ammonium-based compounds, nitrogen-based compounds, vitamins, vitamin C, vitamin B12, folic acid, zinc, amino acids, proteins, nucleic acids, pharmaceutical compounds, 2-heptanal, 2-hexenal, 2-nonenal, 4-decenal, 4-HO-decenal, 4-HO-hexenal, 4-HO-nonenal, 4-HO-octenal, 4 pyrididone-3-carboxy-1-β-D-ribonucleoside, 8-Hydroxy-2'deoxyguanosine, α Keto δ guanidinovlaeric acid, antranilic acid, argininic acid, dimethylarginine, cysteine, decanal, dimethylamine, ethylamine, guanidine, guanidinoacetic acid, guanidine succinic acid, hepatanal, hexanal, hypoxanthine, malondialdehyde, methylguanidine, monomethylamine, neopterine, nicotinamide, N methyl-2-pyridone-5-carboxamide, N-methyl-4-pyridone-3-carboxamide, nonanal, noradrenaline, oxalate, phenylacetic acid, dimethylarginine, trimethylamine, trimethylamine-N-oxide, 3 carboxy-4-methyl-5-propyl-2-furanpropanoic acid, acrolein, carboxymethyllysine, dihydroxyphenylalanine, hippuric acid, homocysteine, indicant, indole-3-acetic acid, indoxyl sulfate, indoxyl-β-D-glucoronide, kynurenic acid, p-cresyl sulfate, pentosidine, phenol, putrescine, permidine, thiocyanate, α1-acid glycoprotein, α1-microglobulin, β-trace protein, β2 microglobulin, adiponectin, angiogenin, calcitonin, complement factor D, cystatin C, fibroblast growth factor-23, glutathione, reduced glutathione, IGF-1, IL-6, IL-8, IL-10, leptin, myoglobin, osteocalcin, parathyroid hormone (PTH), prolactin, resistin, retinal binding protein, soluble intracellular adhesion molecule-1, TNF-α, and vascular endothelial growth factor.

Samples associated with the patient can be a dialysate, or any body fluid taken from the patient, such as blood samples, plasma samples, and/or urine samples.

Based on the results of such analysis, modifying of the first dialysis prescription can involve a change in the prescription relative to the first prescription where longer or shorter dialysis treatment times are prescribed, an increase or decrease in the rate of blood flow through a dialyzer is prescribed, and/or an increase or decrease in the frequency of dialysis treatments is prescribed for the patient.

Further, in embodiments of the system, probes can be inserted into the dialysate waste stream of hemodialysis equipment that can acquire a "Raman signal" or fluid sample that can be used for acquisition of "Raman signal" for the purposes described above. Additionally, complex diagnostic algorithms can be used in conjunction with the Raman data to assess the disease state of individuals suffering acute and chronic organ failure, including kidney failure.

Additional embodiments include automated data collection and analysis systems for processing information from one, two, or more hemodialysis machines simultaneously and providing logical relevant information to hemodialysis personnel for patient management.

Additional embodiments include computational systems and algorithms to relate the levels and interrelationships of various molecules identified by sampling to individual patient health.

In additional embodiments, other samples can be analyzed according to the method of the invention, including, plasma, urine, perfusion fluids, and feces with similar applications and outcomes, with the exception that information would be would be derived from individual patient samples and not analyzed in real-time.

In addition, other uses for these analytical and computational methods described/proposed here that fall within the scope of the invention.

Figure 3:
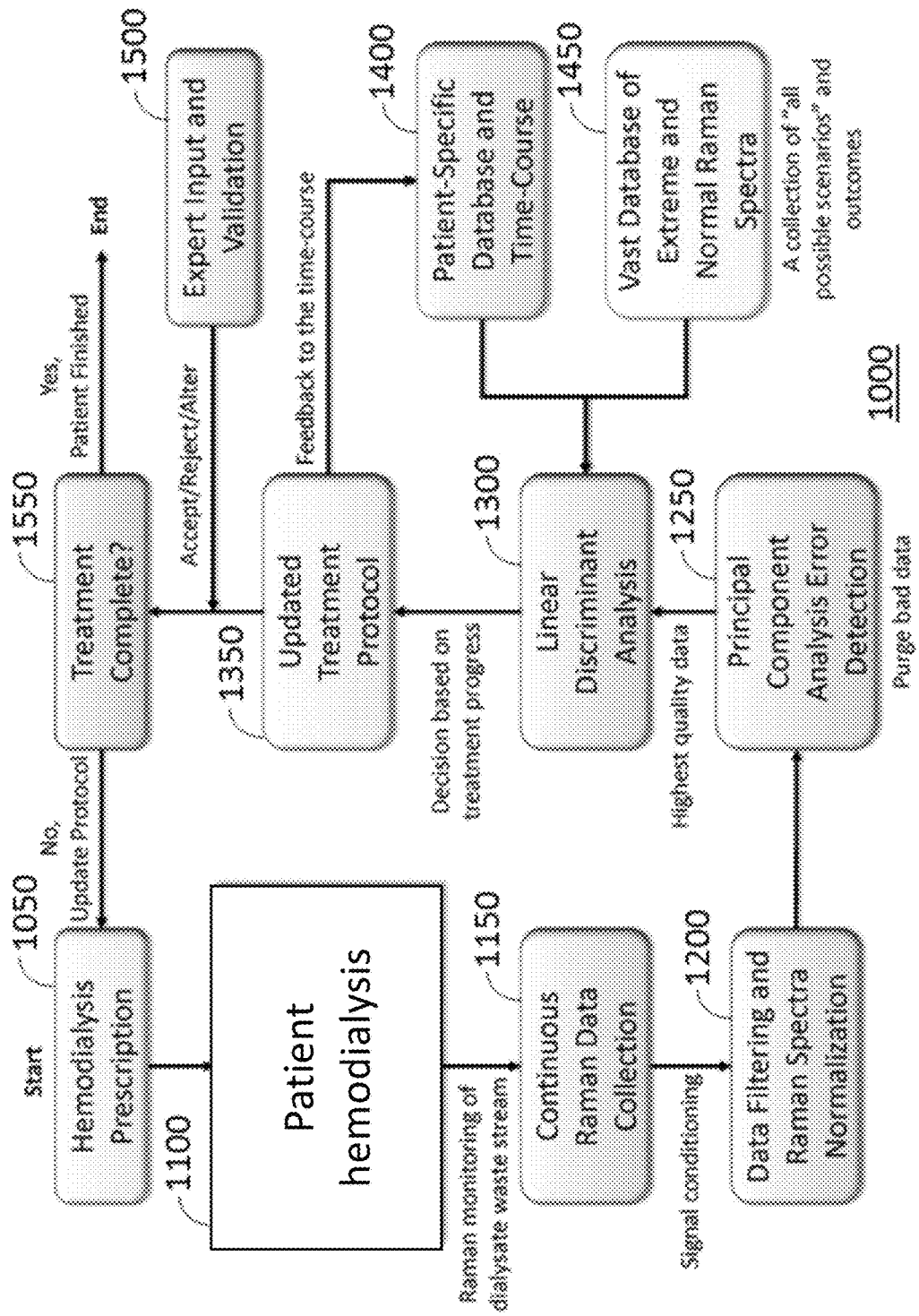
FIG. 3 is a schematic diagram of an embodiment of a method according to the invention.

FIG. 3 is a flowchart that depicts another embodiment of a method 1000 of the invention. As shown, a patient with end-stage renal failure receives a dialysis prescription 1050 and undergoes hemodialysis 1100. The dialysate waste stream is monitored, and Raman spectrometry data is continuously collected 1150. The Raman data undergoes signal conditioning during which the data is filtered and the Raman spectra normalized 1200. A principle components analysis error detection method is optionally used to purge bad data 1250 so that only the highest quality data is retained. A linear discriminant analysis is optionally used on the retained data 1300 to monitor the hemodialysis treatment progress. The linear discriminant analysis 1300 evaluates treatment progress based on a comparison between a vast database of extreme and normal Raman spectra 1450 which provide a collection of all possible scenarios and outcomes, along with a patient-specific database and time-course 1400. As a result, a decision is made based on treatment progress and results in an updated treatment protocol 1350, which feeds back to the patient-specific time course 1400. An expert clinician 1500 provides expert input and validation to accept, reject, or alter the updated treatment protocol. At this time, it is determined whether treatment is complete 1550—if yes, the hemodialysis is finished, and if no, the treatment protocol is updated, and then fed back into the hemodialysis prescription 1050.

Figure 4:
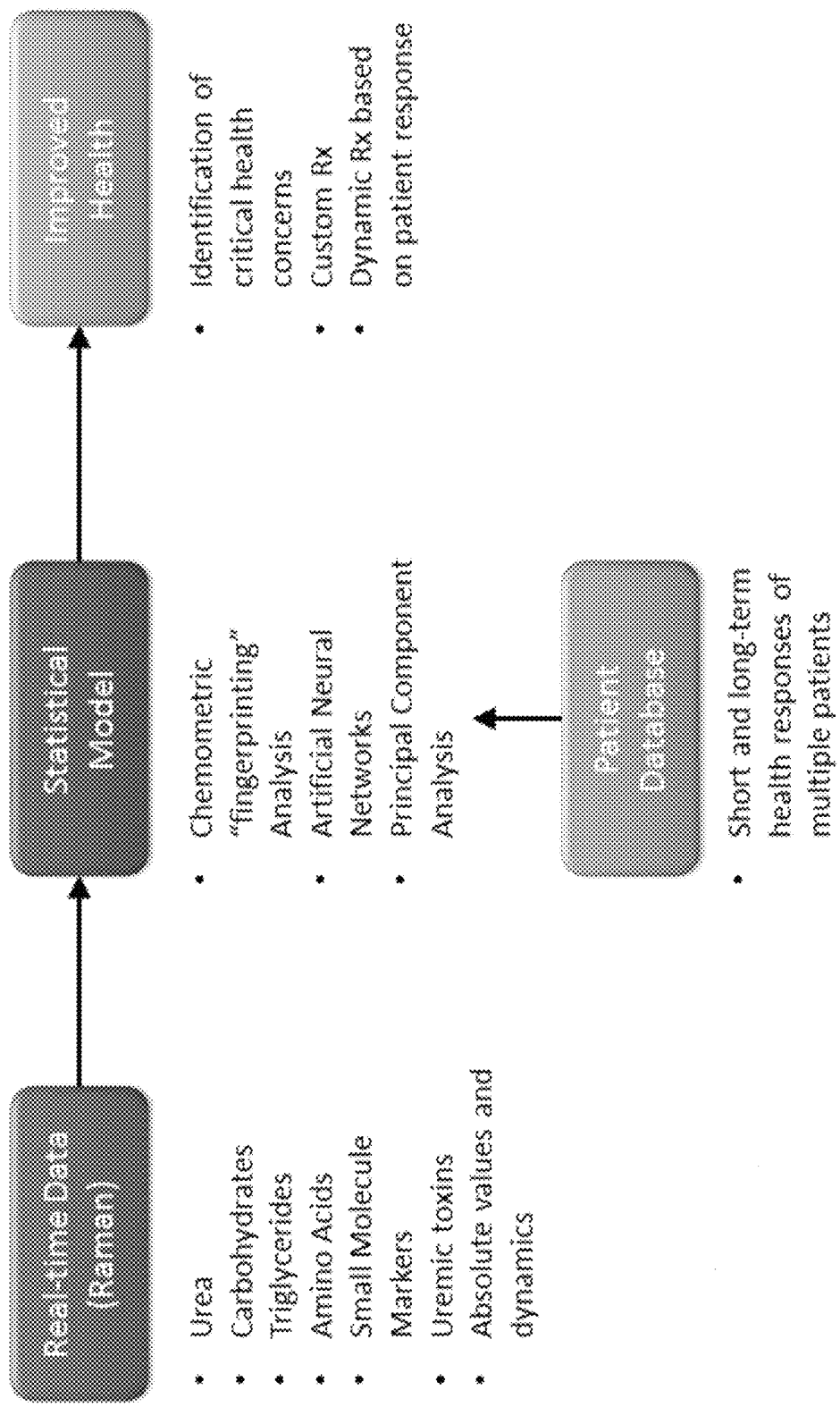
FIG. 4 is a flowchart showing an embodiment of a method of the invention.

Similar to FIG. 3, FIG. 4 is a flow chart showing an embodiment of a method of the invention. First, real-time measurements of Raman spectra of target analytes are obtained, including target analytes such as one or more of urea, carbohydrates, triglycerides, amino acids, small molecule markers, and/or uremic toxins. The measurements include absolute values and dynamics. The spectra are fed into a statistical model, which can include CHEMOMETRIC FINGERPRINTING™ analysis, and algorithms such as artificial neural networks and principal components analysis. Values from a patient database of short and long-term health responses of multiple patients may be incorporated into the statistical model. As a result of the statistical model, critical health concerns may be identified or a custom dialysis prescription or a dynamic dialysis prescription based on patient response may be generated.

It will be understood that some or all of the method steps described in this specification may be carried out by a group of computer-executable instructions that may be organized into routines, subroutines, procedures, objects, methods, functions, or any other organization of computer-executable instructions that is known or becomes known to a skilled artisan in light of this disclosure, where the computer-executable instructions are configured to direct a computer or other data processing device such as a processor to perform one or more of the specified processes and operations. The computer-executable instructions may be written in any suitable programming language or languages, including C, C++, C#, Visual Basic, Java, Python, Perl, PHP, Html, CSS, and JavaScript.

In other embodiments of the invention, files comprising the set of computer-executable instructions may be stored in computer-readable memory on a single computer or distributed across multiple computers. A skilled artisan will further appreciate, in light of this disclosure, how the invention can be implemented, in addition to software, using hardware or firmware. As such, as used herein, the operations of the invention can be implemented in a system comprising any combination of software, hardware, or firmware.

Embodiments of the invention also include a non-transitory computer readable medium comprising one or more computer files comprising a set of computer-executable instructions for performing one or more of the calculations, steps, processes and operations described and/or depicted herein. In exemplary embodiments, the files may be stored contiguously or non-contiguously on the computer-readable medium. Embodiments may include a computer program product comprising the computer files, either in the form of the computer-readable medium comprising the computer files and, optionally, made available to a consumer through packaging, or alternatively made available to a consumer through electronic distribution. As used in the context of this specification, a "computer-readable medium" includes any kind of computer memory such as floppy disks, conventional hard disks, CD-ROM, Flash ROM, non-volatile ROM, electrically erasable programmable read-only memory (EEPROM), and RAM. In exemplary embodiments, the computer readable medium has a set of instructions stored thereon which, when executed by a processor, cause the processor to perform the steps described in this specification. The processor may implement this process through any of the procedures discussed in this disclosure or through any equivalent procedure.

For example, one embodiment of the invention includes one or more non-transitory computer-readable media, at least one having one or more reference sets of a plurality of Raman spectra of one or more target analytes stored thereon, wherein the reference sets represent one or more dialysis treatment outcome characteristics, and at least one having a set of computer-executable instructions stored thereon that direct a computer to a) receive spectra from a Raman spectrometer of the one or more target analytes obtained from a sample from a dialysis patient, b) analyze the received Raman spectra with a processor according to an algorithm, wherein the analysis is based on a comparison of the received Raman spectra with the plurality of Raman spectra stored on the non-transitory computer-readable media, and c) determine a dialysis treatment outcome characteristic of the dialysis patient based on the analysis.

Another embodiment of the invention includes a non-transitory computer-readable medium having a set of computer-executable instructions stored thereon that direct a computer to a) receive spectra from a Raman spectrometer of one or more target analytes obtained from a first sample from a dialysis patient at a first time point, b) store the received spectra in memory, c) receive spectra from a Raman spectrometer of one or more target analytes obtained from a second sample from the dialysis patient at a second later time point, d) compare the spectra from the second time point with the spectra from the first time point with a processor, and e) determine a dialysis treatment outcome characteristic of the dialysis patient based on the comparison.

In other embodiments of the invention, files comprising the set of computer-executable instructions may be stored in computer-readable memory on a single computer or distributed across multiple computers. A skilled artisan will further appreciate, in light of this disclosure, how the invention can be implemented, in addition to software, using hardware or firmware. As such, as used herein, the operations of the invention can be implemented in a system comprising any combination of software, hardware, or firmware Embodiments of the invention include one or more computers or devices loaded with a set of the computer-executable instructions described herein. The computers or devices may be a general purpose computer, a special-purpose computer, or other programmable data processing apparatus to produce a particular machine, such that the one or more computers or devices are instructed and configured to carry out the calculations, processes, steps, and operations of the invention. The computer or device performing the specified calculations, processes, steps, and operations may comprise at least one processing element such as a central processing unit (i.e. processor) and a form of computer-readable memory which may include random-access memory (RAM) or read-only memory (ROM). The computer-executable instructions can be embedded in computer hardware or stored in the computer-readable memory such that the computer or device may be directed to perform one or more of the processes and operations depicted and/or described herein. The computers or devices may include one or more of the databases described herein stored in computer memory. The computers or devices may be connected to a Raman spectrometer described herein through a wired or wireless connection.

Additional embodiments of the invention comprise a computer system for carrying out the methods of the invention. The computer system may comprise a processor for executing the computer-executable instructions, one or more databases described herein, a user interface, and a set of instructions (e.g. software) for carrying out the method. The computer system can be a stand-alone computer, such as a desktop computer, a portable computer, such as a tablet, laptop, PDA, or smartphone, or a set of computers connected through a network including a client-server configuration and one or more database servers. The network may use any suitable network protocol, including IP, UDP, or ICMP, and may be any suitable wired or wireless network including any local area network, wide area network, Internet network, telecommunications network, Wi-Fi enabled network, or Bluetooth enabled network.

Embodiments of the invention include a system comprising a Raman spectrometer comprising a laser, a spectrometer, and a fiber optic probe, and a computer comprising an input/output device, a processor, and a memory operably connected to the Raman spectrometer. In this embodiment, the fiber optic probe is adapted to continuously measure a dialysate waste stream from a hemodialysis machine. In one embodiment, to continuously measure the dialysate involves taking measurements at selected time intervals, and preferably automatically or pre-programmed to take measurements at selected times. The memory has one or more reference sets of a plurality of Raman spectra of one or more target analytes stored thereon, wherein the reference sets represent one or more dialysis treatment outcome characteristics. In this embodiment, the laser is configured to excite one or more target analytes in the dialysate waste stream which correspond to the one or more target analytes of the reference sets at a wavelength that produces Raman spectra.

Example

Six patients (three male and three female) with a differing history of hemodialysis (first instance to 6 years) were the subject of a study for measuring the kinetics of target analytes during a hemodialysis treatment using Raman spectroscopy. Dialysate samples were collected at beginning (A), middle (B), and end (C) of the prescription cycle (Samples A, B, and C). All patients were dialyzed against G2231 dialysate and OPTIFLUX® High Fluid Coil dialyzer. There was no significant variation in total prescription time (221-244 minutes). No significant variation in eating was observed. One patient (Patient #1) was a known diabetic. Characteristics of the dialysis patients are shown in the table in FIG. 5.

For analysis, 500 µL of a sample associated with a patient was placed on a foil tray, and allowed to air dry. This dried sample was analyzed using the Bruker Senterra Raman microscope. Comparisons were made between "dried" and "liquid" phase measurements. Correlations were already established between Raman bands and experimentally measured amino acids (UPLC) and fatty acids (GC-MS). Standards were used for urea and bicarbonate. Literature data are available for carbohydrates and small molecules. The Raman Spectra obtained from the OPUS software was processed in Matlab software to normalize the data, and average the spectra of each sample. These were then plotted in Excel. Results of the experiment fall into two categories, Discriminate Analysis and Peak Analysis.

Peak Analysis was conducted to identify specific peaks of interest, which correlate to specific chemical compounds that dialysis should be affecting. Exemplary peaks of interest include Urea (~1000 $cm^{-1}$), Sodium Bicarbonate (~1040 $cm^{-1}$), Glucose/Fatty Acids/Triglycerides (~1070 $cm^{-1}$), and Carbohydrates (~930 $cm^{-1}$).

Figure 6:
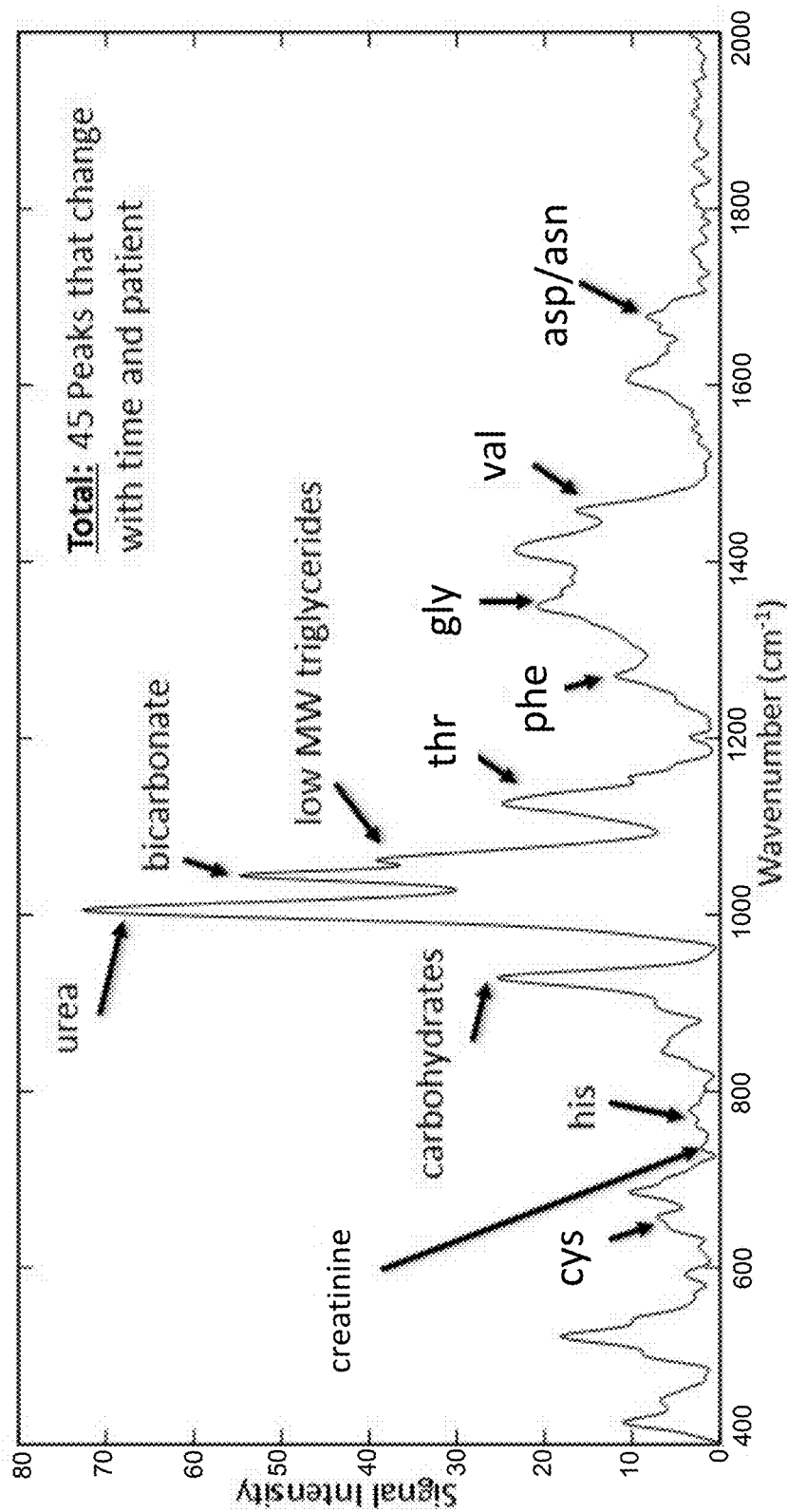
FIG. 6 is a graph of a Raman spectrum annotated to show characteristic peaks of representative target analytes.

FIG. 6 is an example of a Raman spectrum obtained in this Example. Forty five peaks were identified that change with time and the patient.

Figure 7:
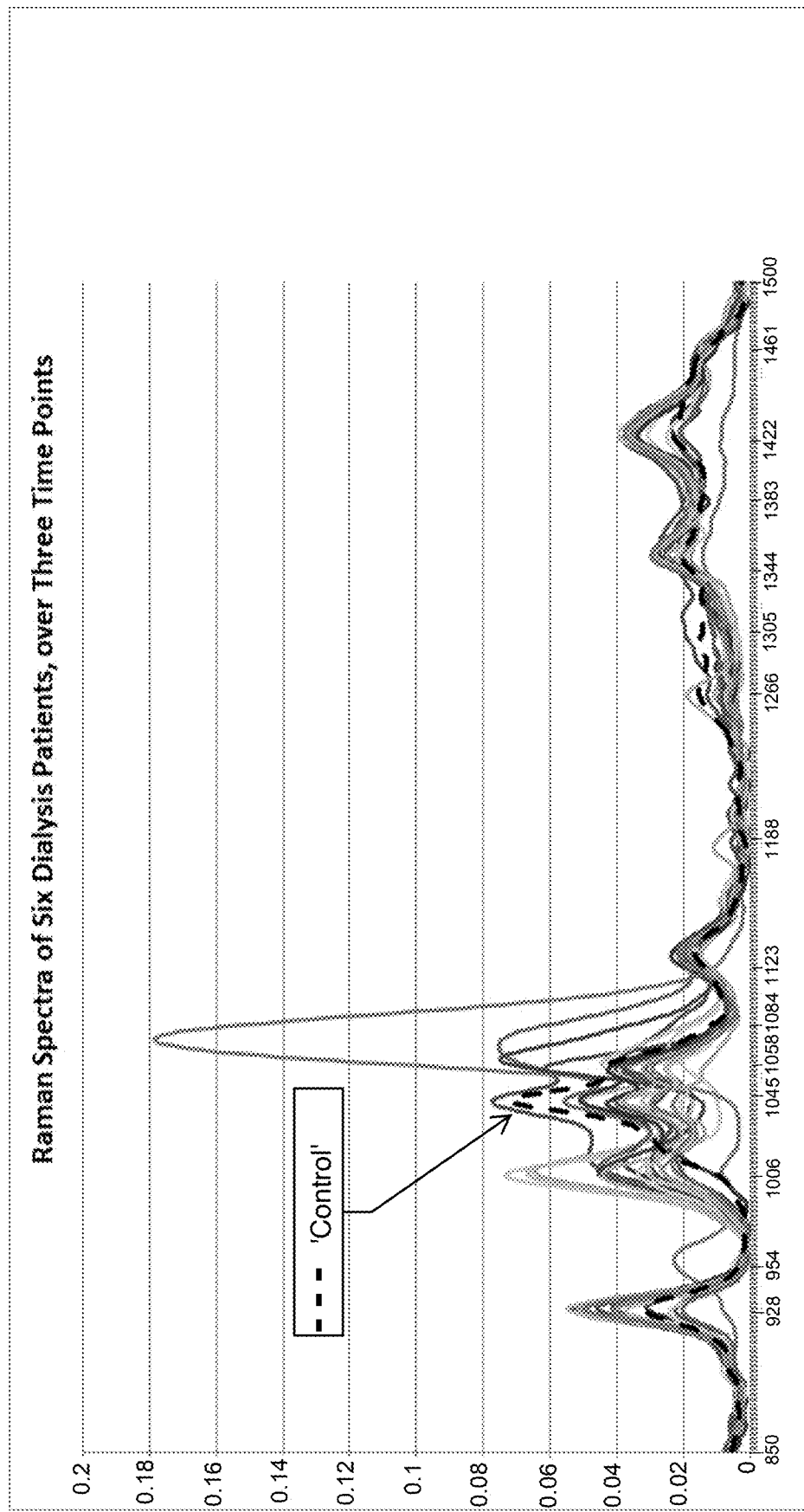
FIG. 7 is a graph of Raman spectra of the six dialysis patients over three time points relative to a control sample.
Figure 8A:
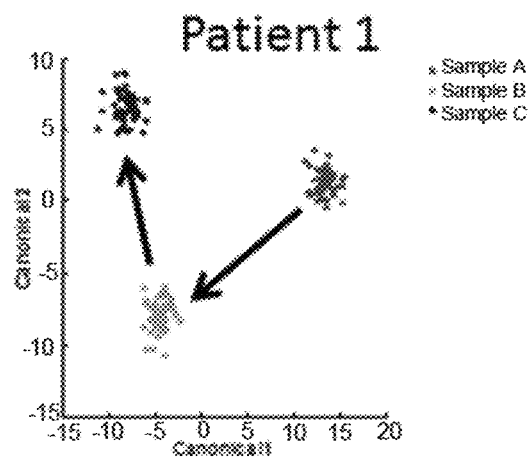
FIGS. 8A-8F are graphs showing the results of Discriminate Analysis for each patient 1-6, respectively.
Figure 8B:
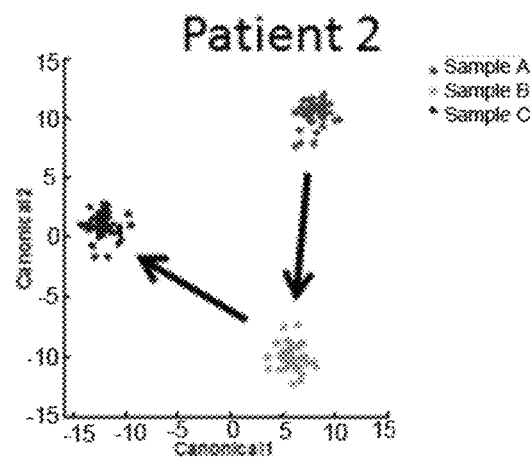
Figure 8C:
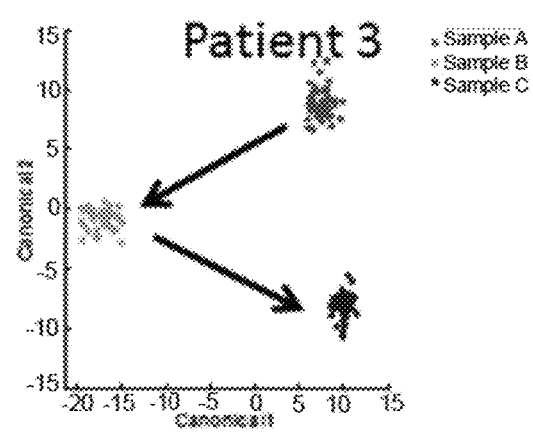
Figure 8D:
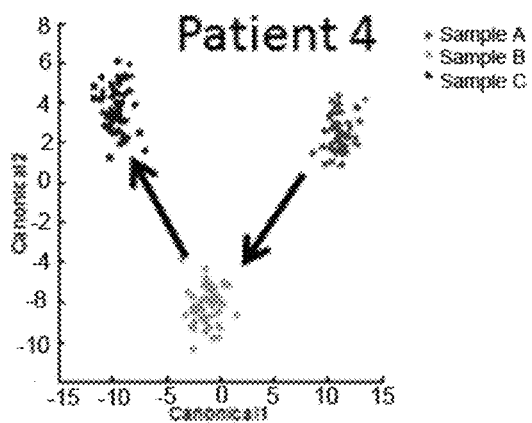
Figure 8E:
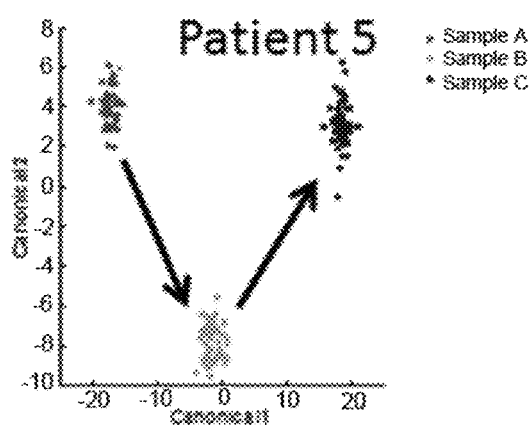
Figure 8F:
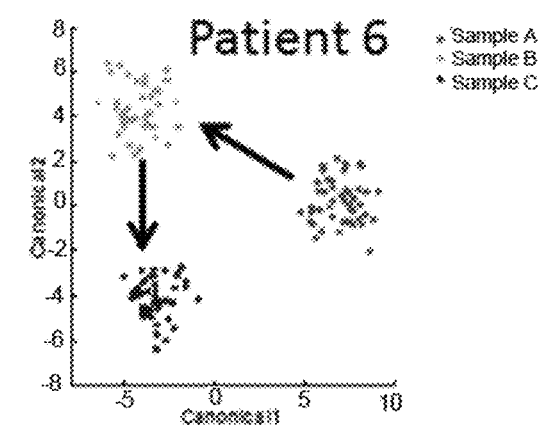
Figure 9A:
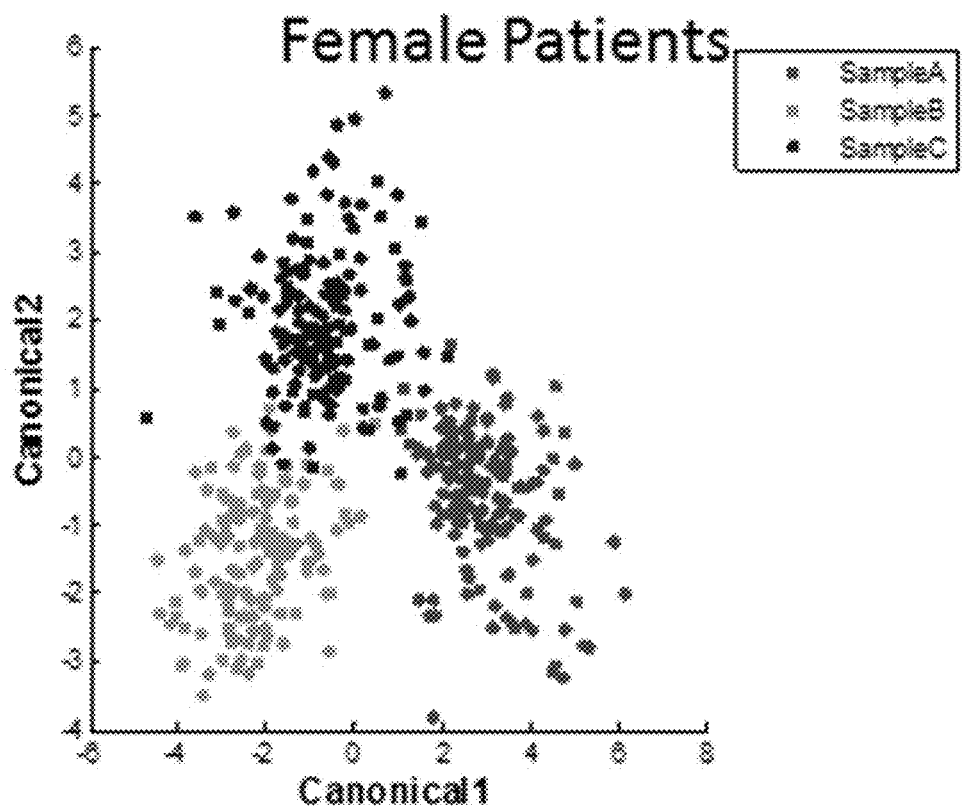
FIGS. 9A and 9B are graphs showing the results of Discriminate Analysis for male and female patients, respectively.
Figure 9B:
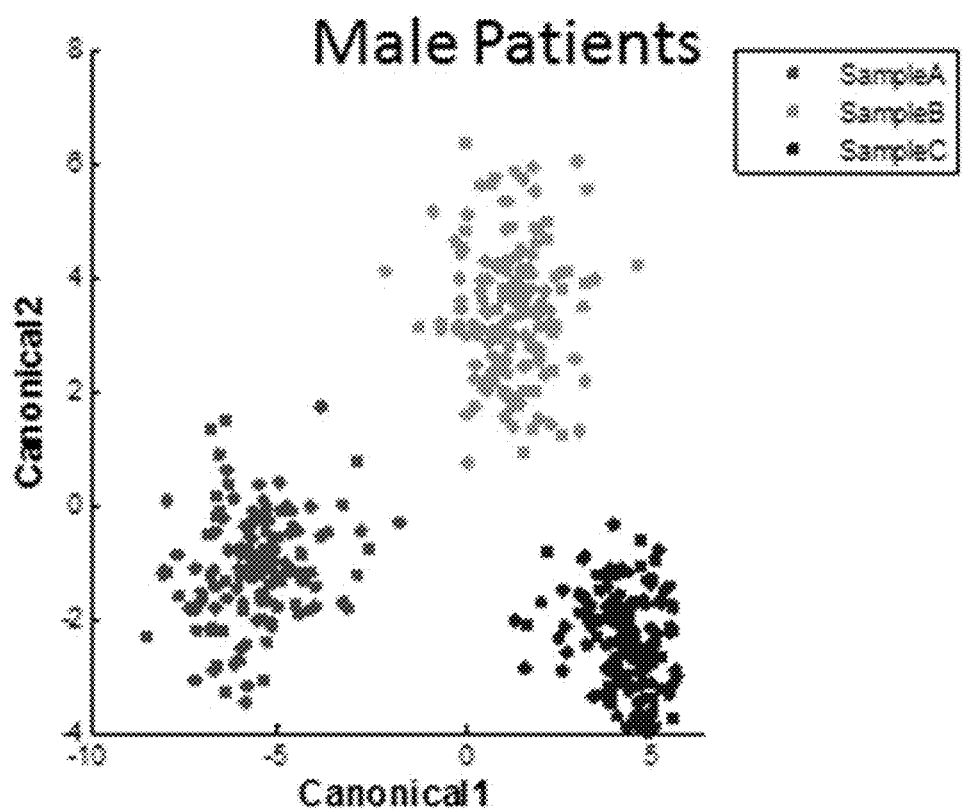
Figure 10A:
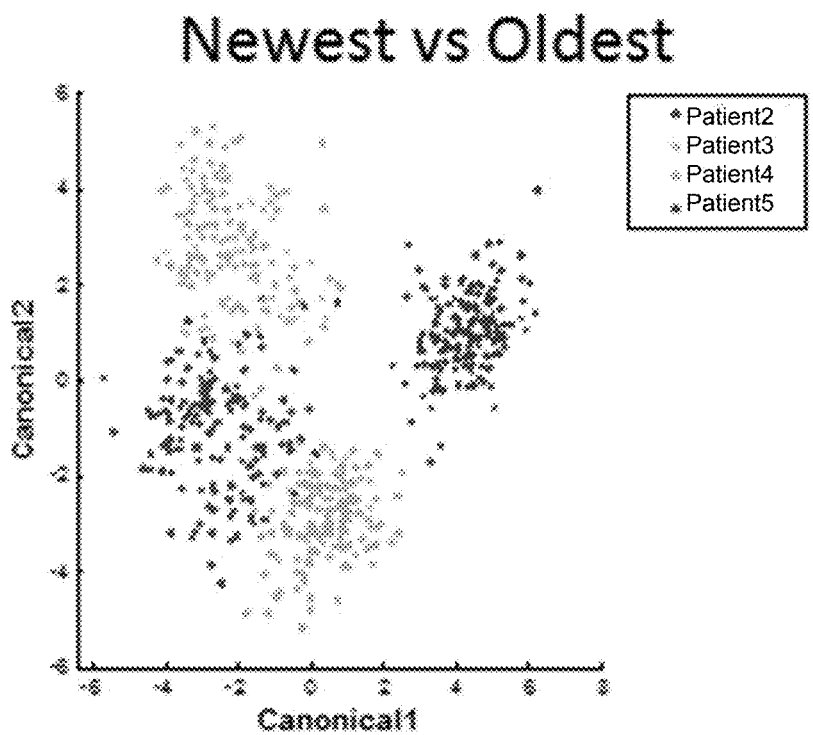
FIGS. 10A and 10B are graphs showing the results of Discriminate Analysis for all of the samples for Patients 2-5 and Patients 4-5, respectively.
Figure 10B:
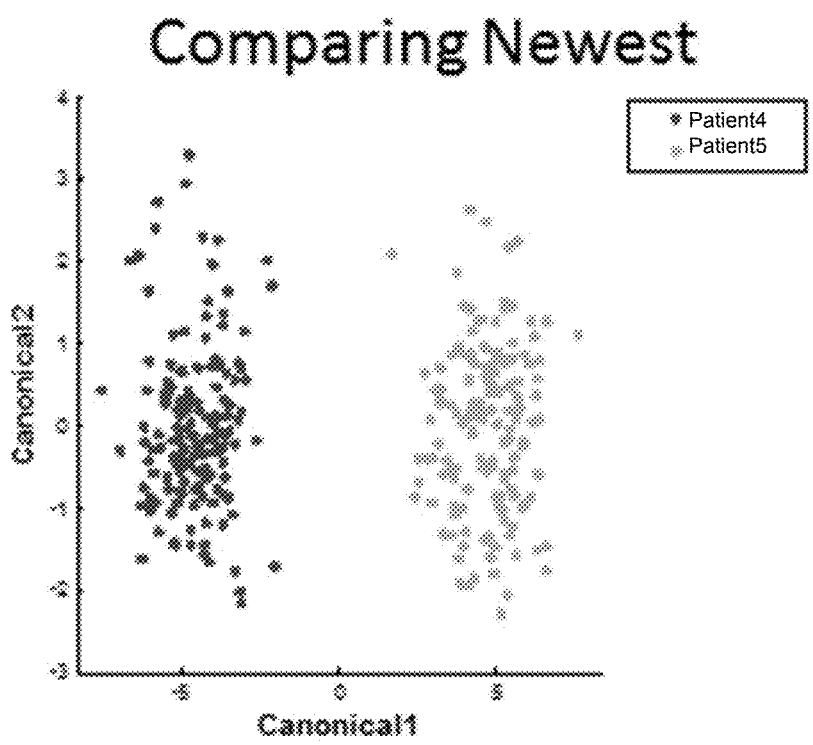

FIG. 7 shows Raman spectra of the six dialysis patients over the three time points relative to a control sample. These spectra were subject to Discriminate Analysis. The results of Discriminate Analysis for each patient are shown in FIGS. 8A-8F. Due to the limited time points, as well as limited knowledge of the time interval between samples, it is difficult to determine a mathematical relationship between the Patient samples. However, the relative diffusivity of the clusters may allow for further analysis. FIGS. 9A and 9B show the results of analysis by gender, which did reveal differences between the distinctiveness of the clusters. This could signify differences in effectiveness of the treatment determined by gender. FIGS. 10A and 10B show a Discriminate Analysis of all the samples, which did show difference from the control, as well as from one another. This was true based on history of hemodialysis, gender, and through each of the time points.

Figure 11:
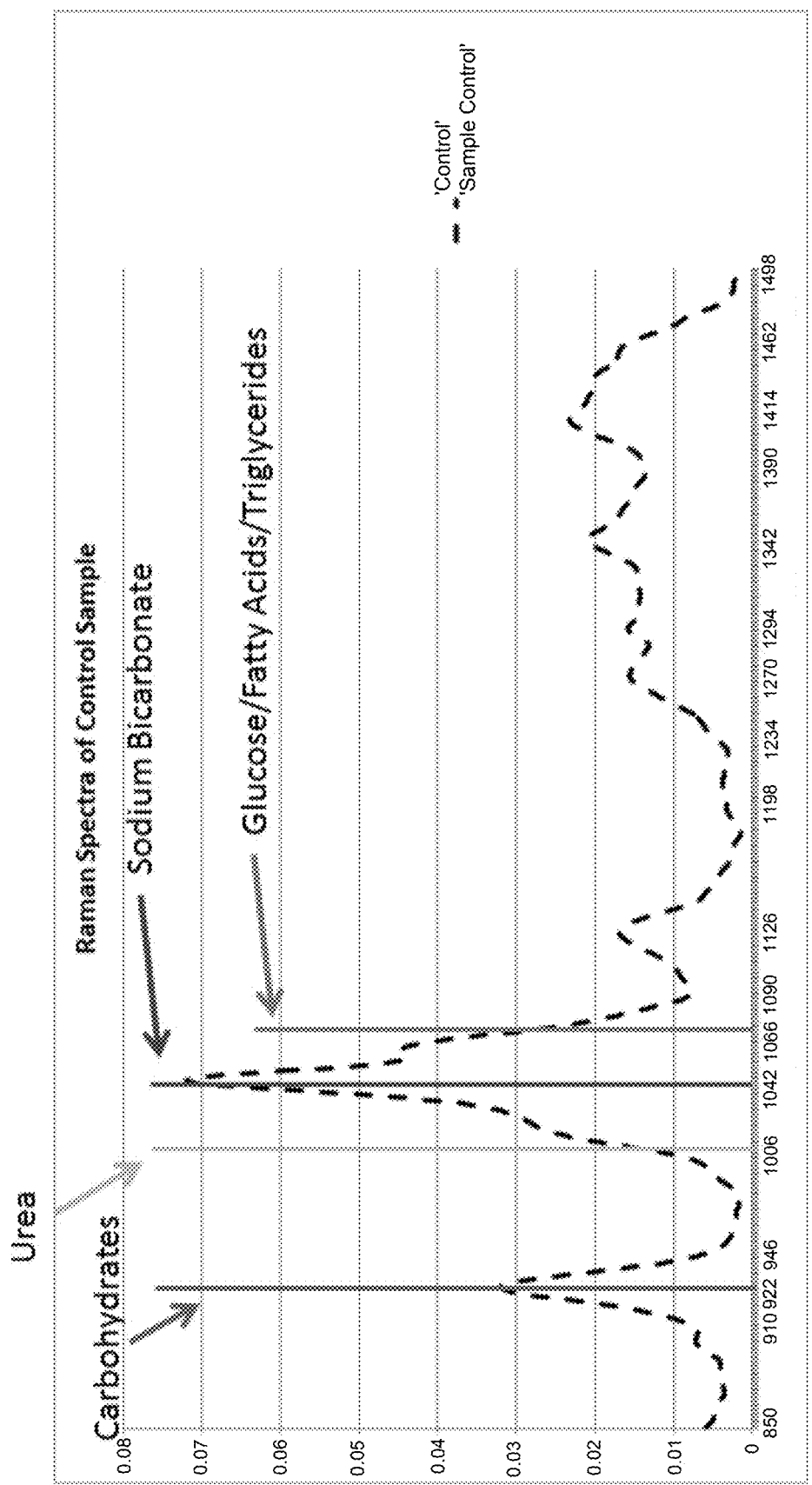
FIG. 11 is a graph of a Raman spectrum of a Control Sample showing Peak Analysis.
Figure 12:
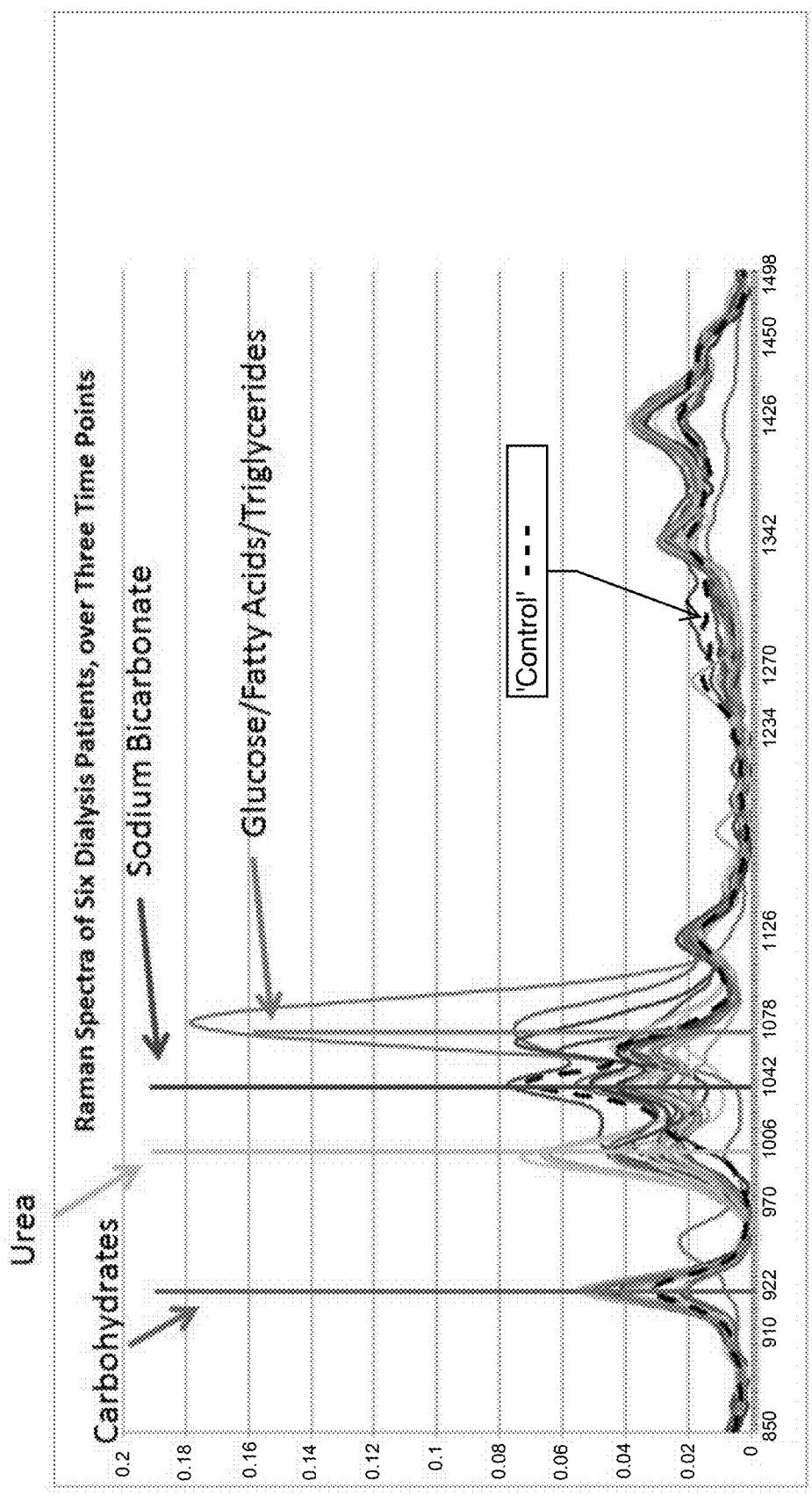
FIG. 12 a graph of Raman spectra obtained from the six dialysis patients at three time points relative to control showing Peak Analysis.
Figure 13:
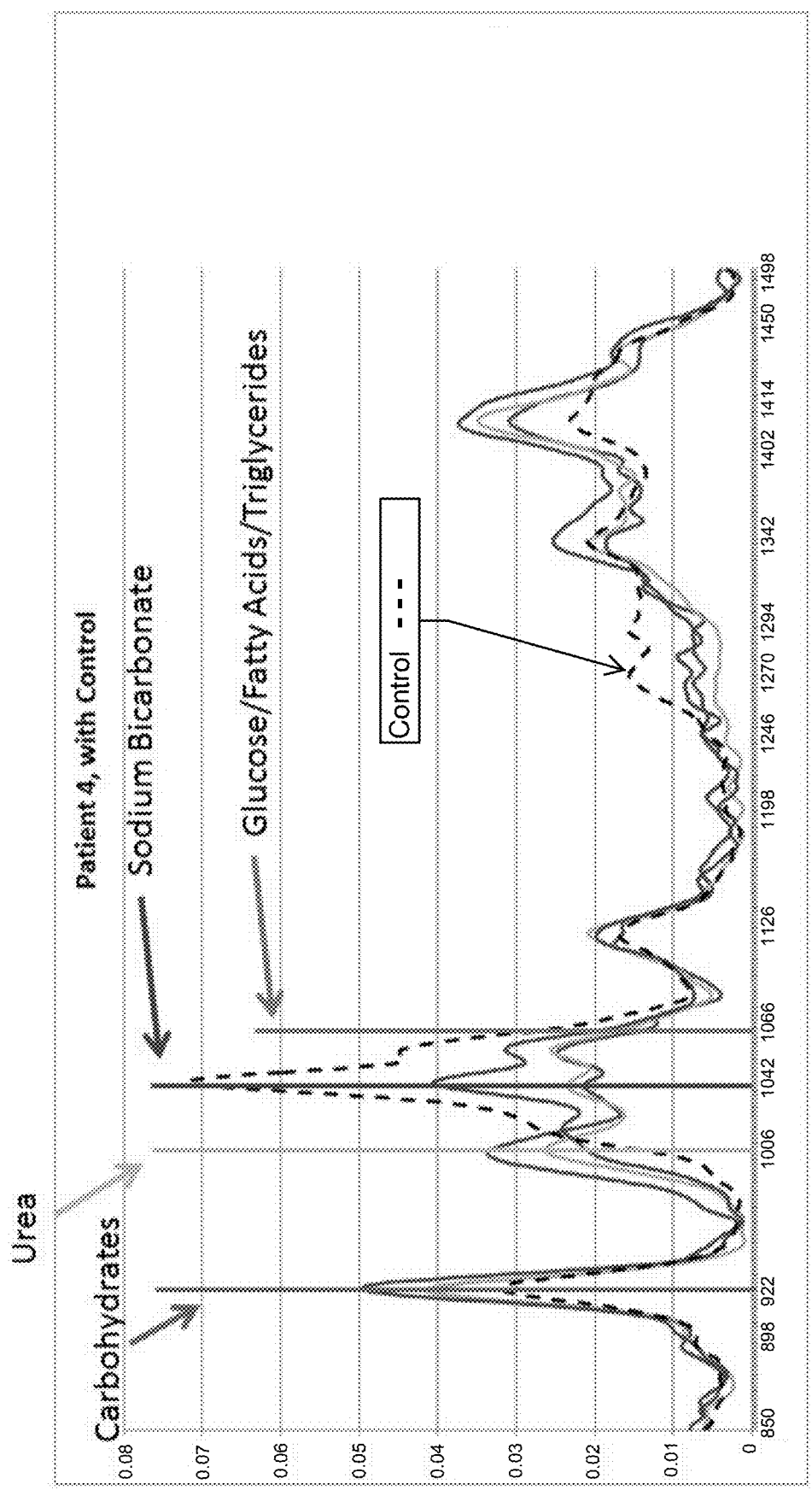
FIG. 13 is a graph of a Raman spectra of Patient 4 over three time points showing Peak Analysis.

FIG. 11 shows the results of Peak Analysis of a Control Sample. The control sample shows no peaks characteristic of urea or glucose. FIG. 12 shows the result of peak analysis for all spectra obtained from the six dialysis patients at the three time points relative to control. The annotated spectra in FIGS. 11 and 12 show the peaks characteristic for carbohydrates, urea, sodium bicarbonate, and glucose/fatty acids/triglycerides. FIG. 13 shows the results of Peak Analysis for an individual patient (Patient 4) over the three time points.

Figures 14A, 14B:
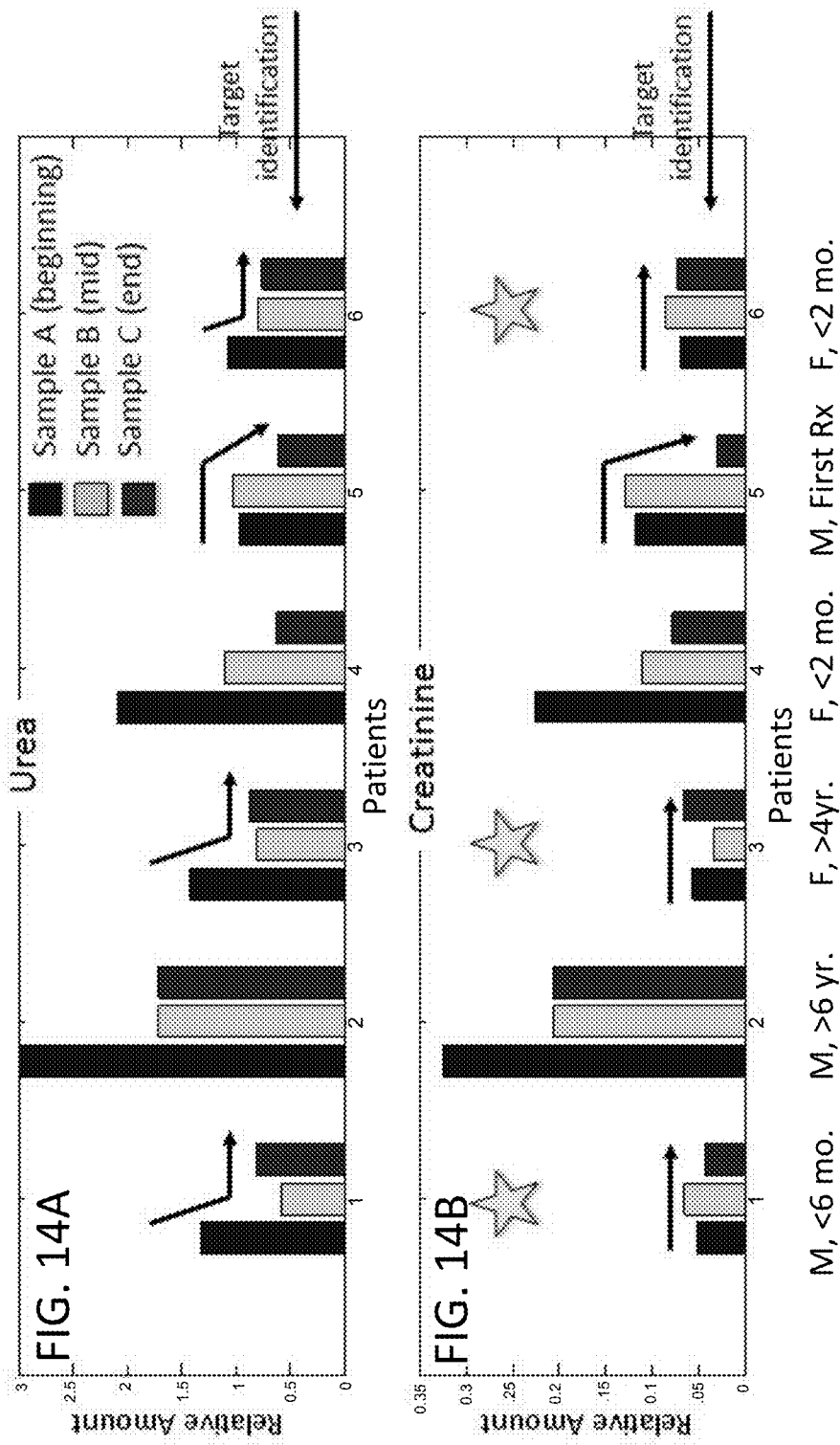
FIGS. 14-20 are graphs showing the kinetics of different target analyte clearances over three time points during the hemodialysis treatment for each of the six patients, with FIGS. 14A and 14B comparing urea clearances with that of creatinine, FIG. 15 showing carbohydrate modulation, FIG. 16 showing low MW triglyceride clearances, FIG. 17 showing glycine secretion, FIG. 18 showing aspartic acid/asparagine modulation, FIG. 19 showing glutamic acid/glutamine modulation, and FIG. 20 showing sodium bicarbonate secretion.
Figure 15:
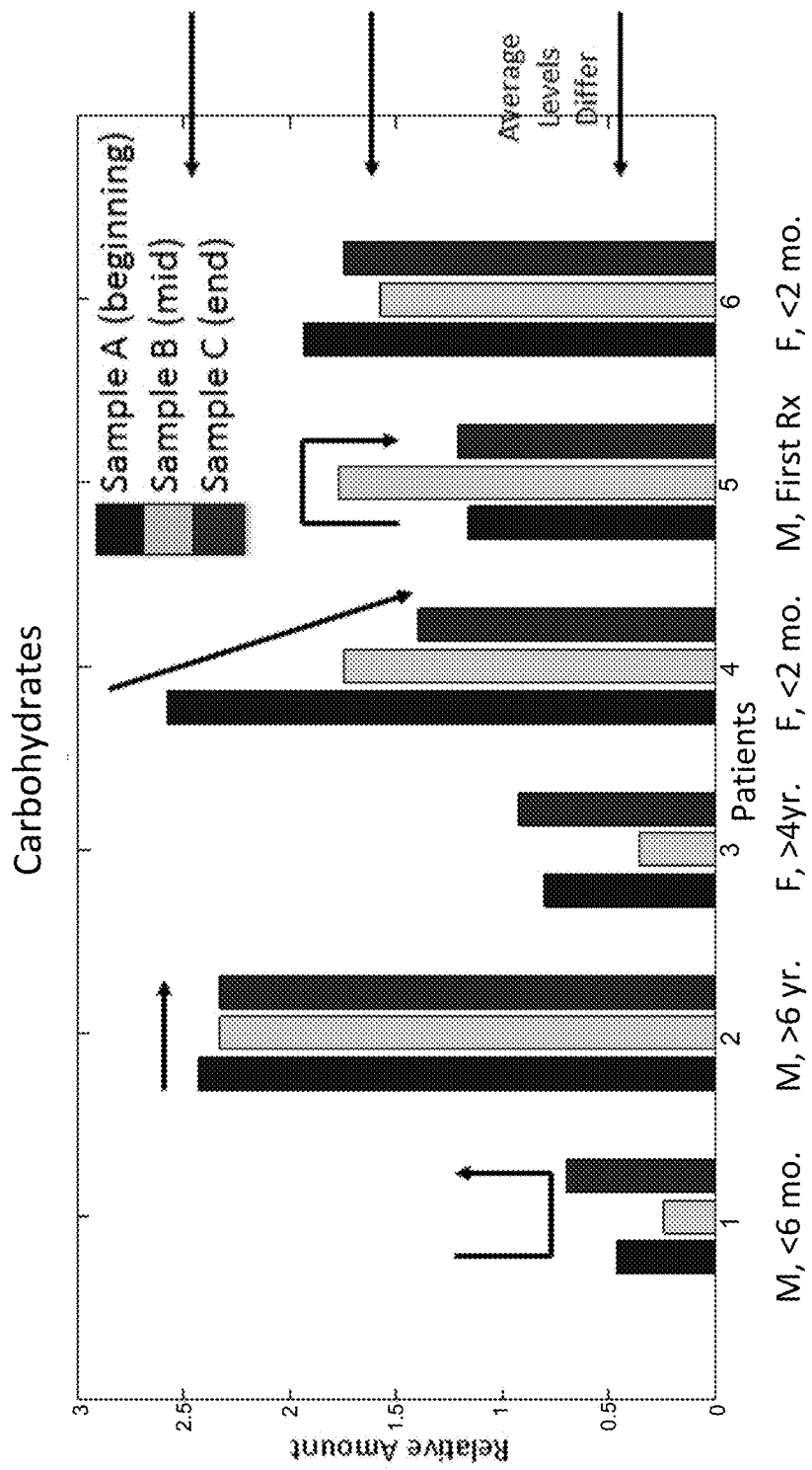
Figure 16:
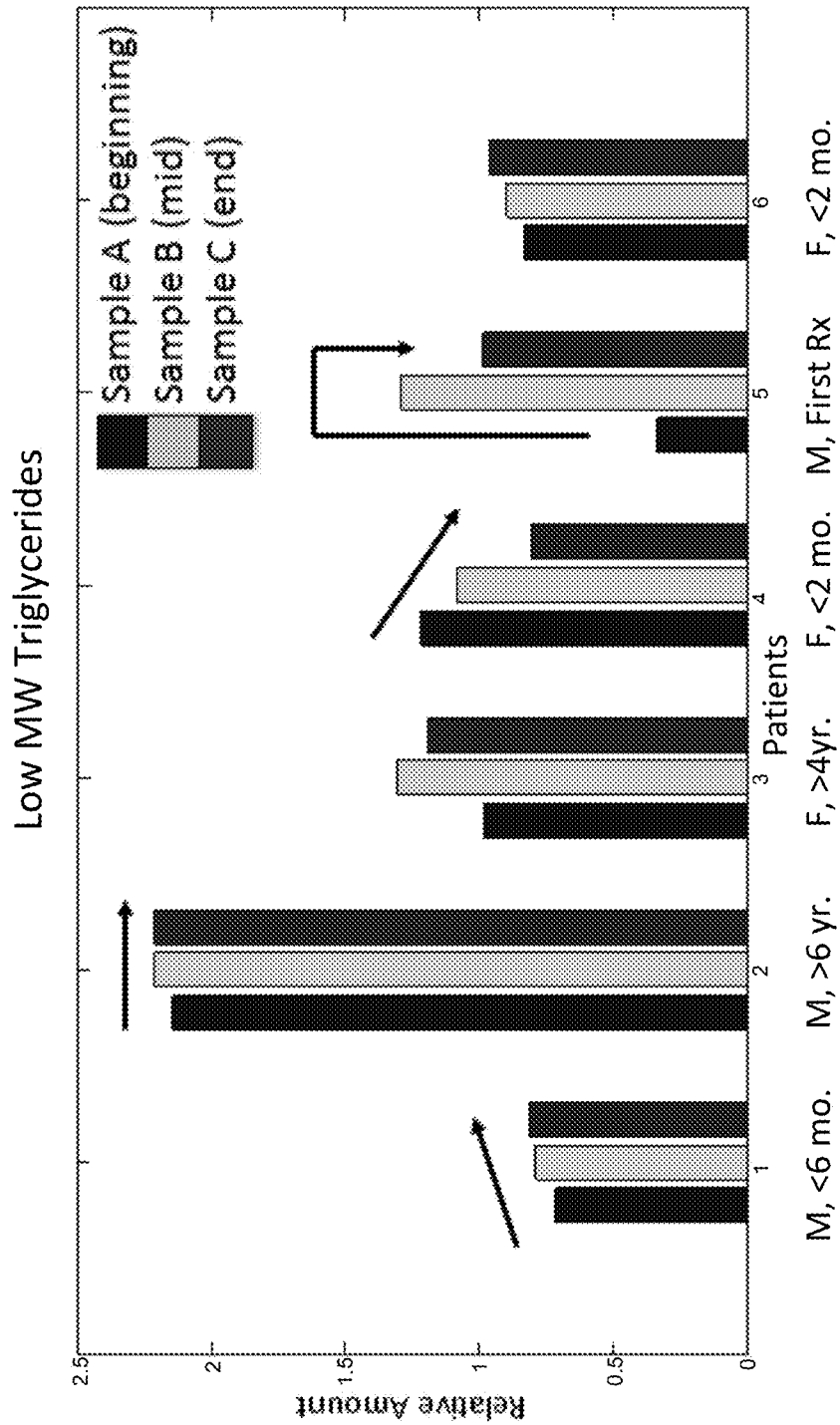
Figure 17:
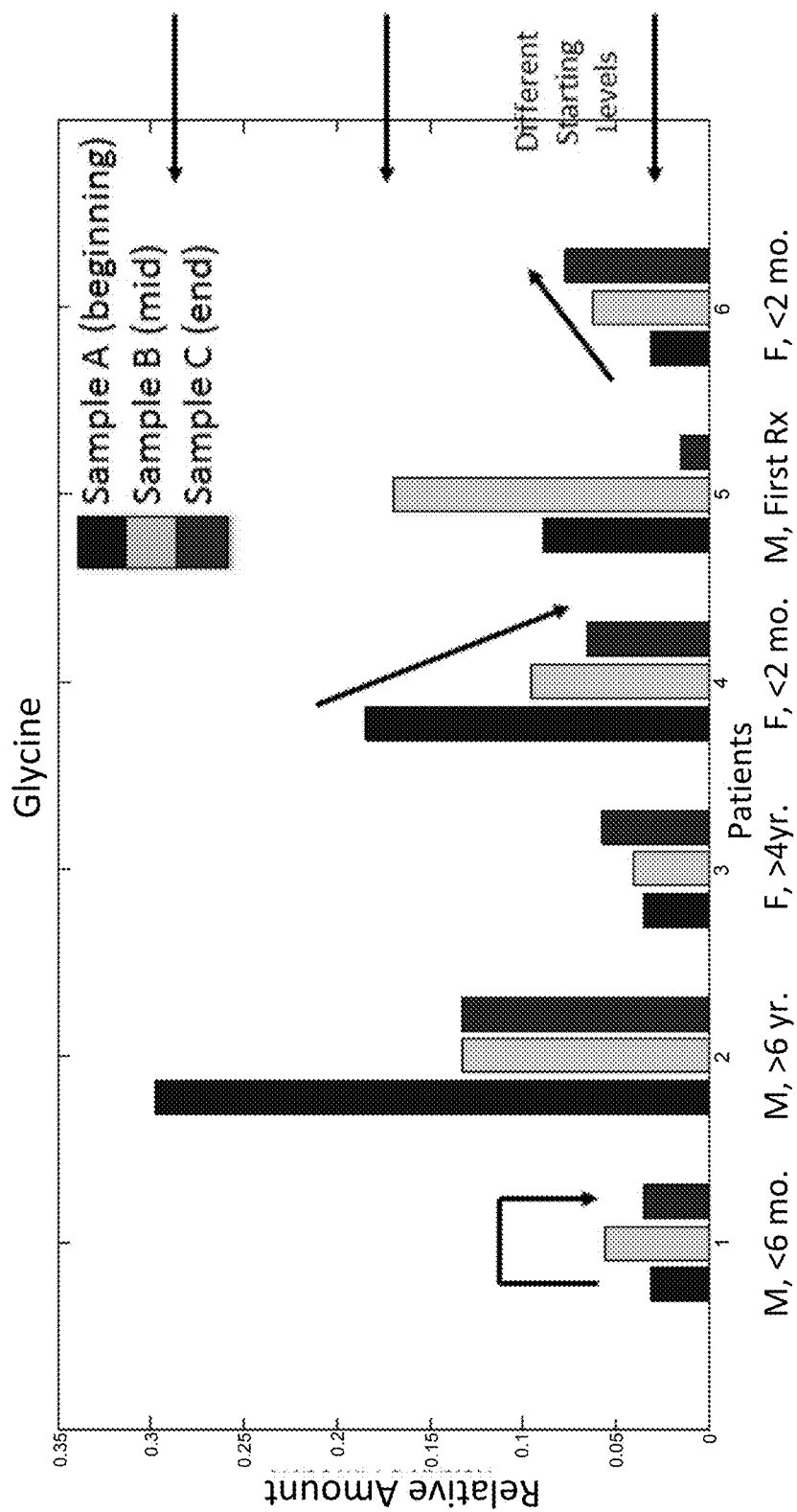
Figure 18:
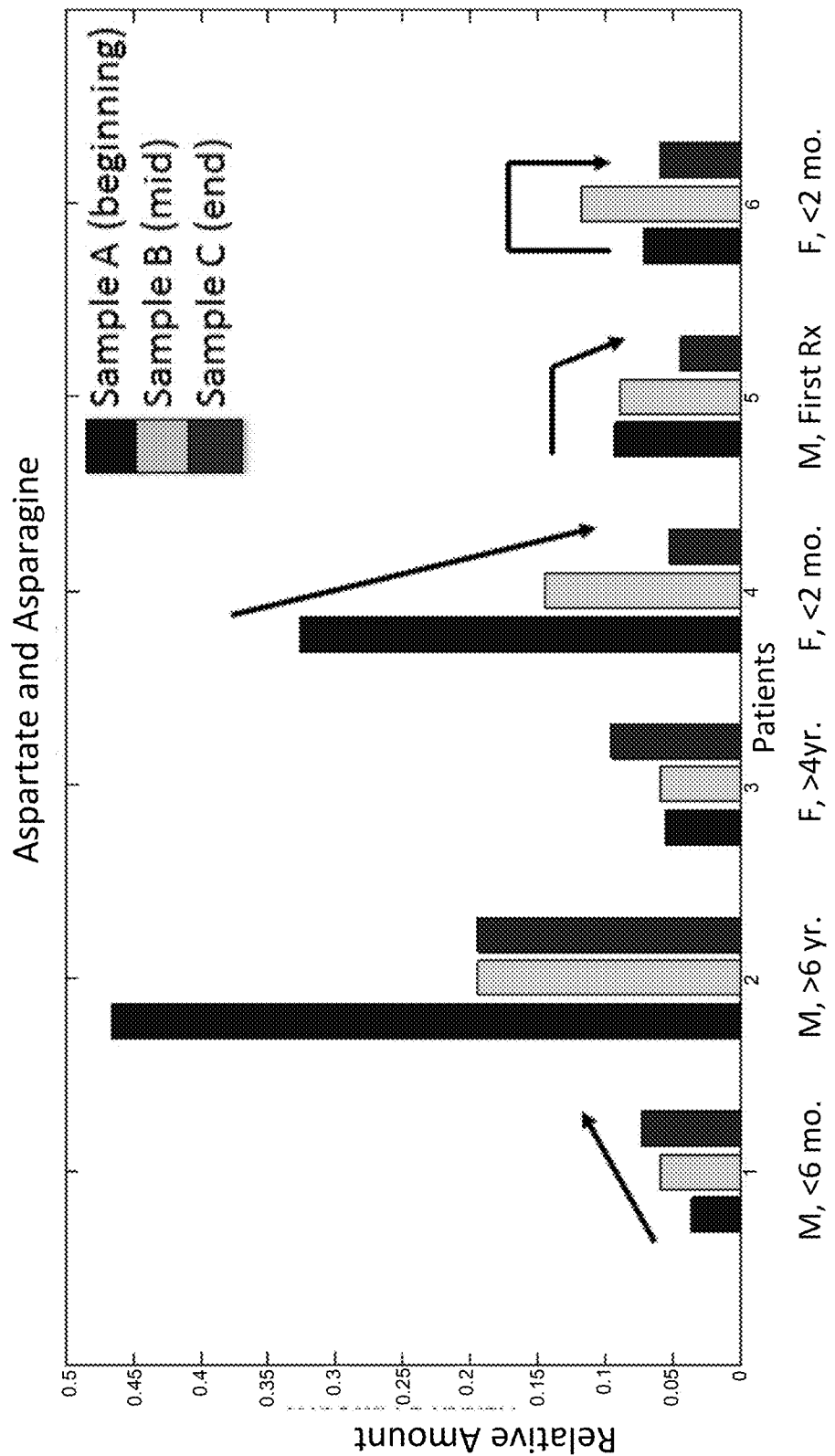
Figure 19:
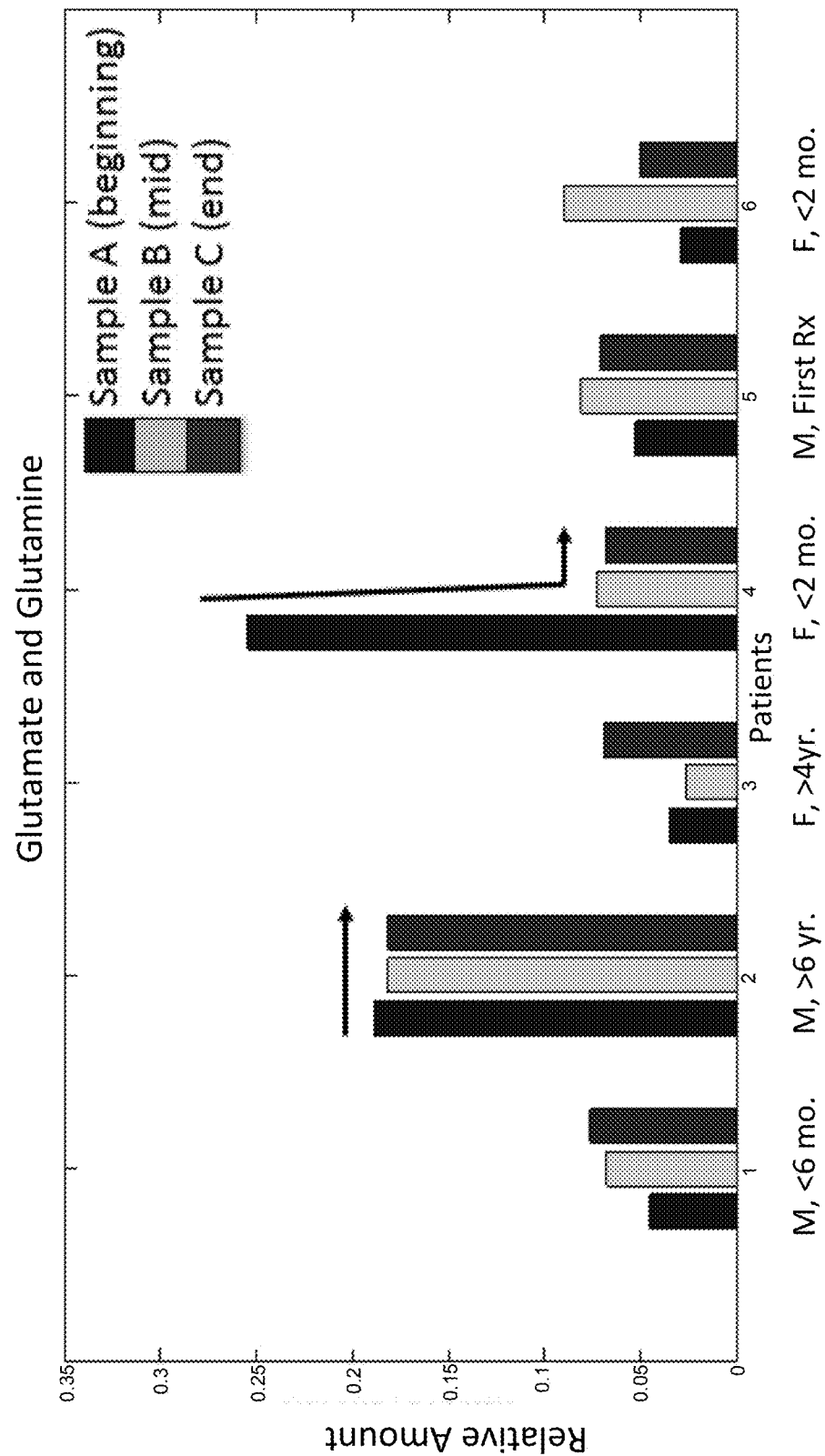
Figure 20:
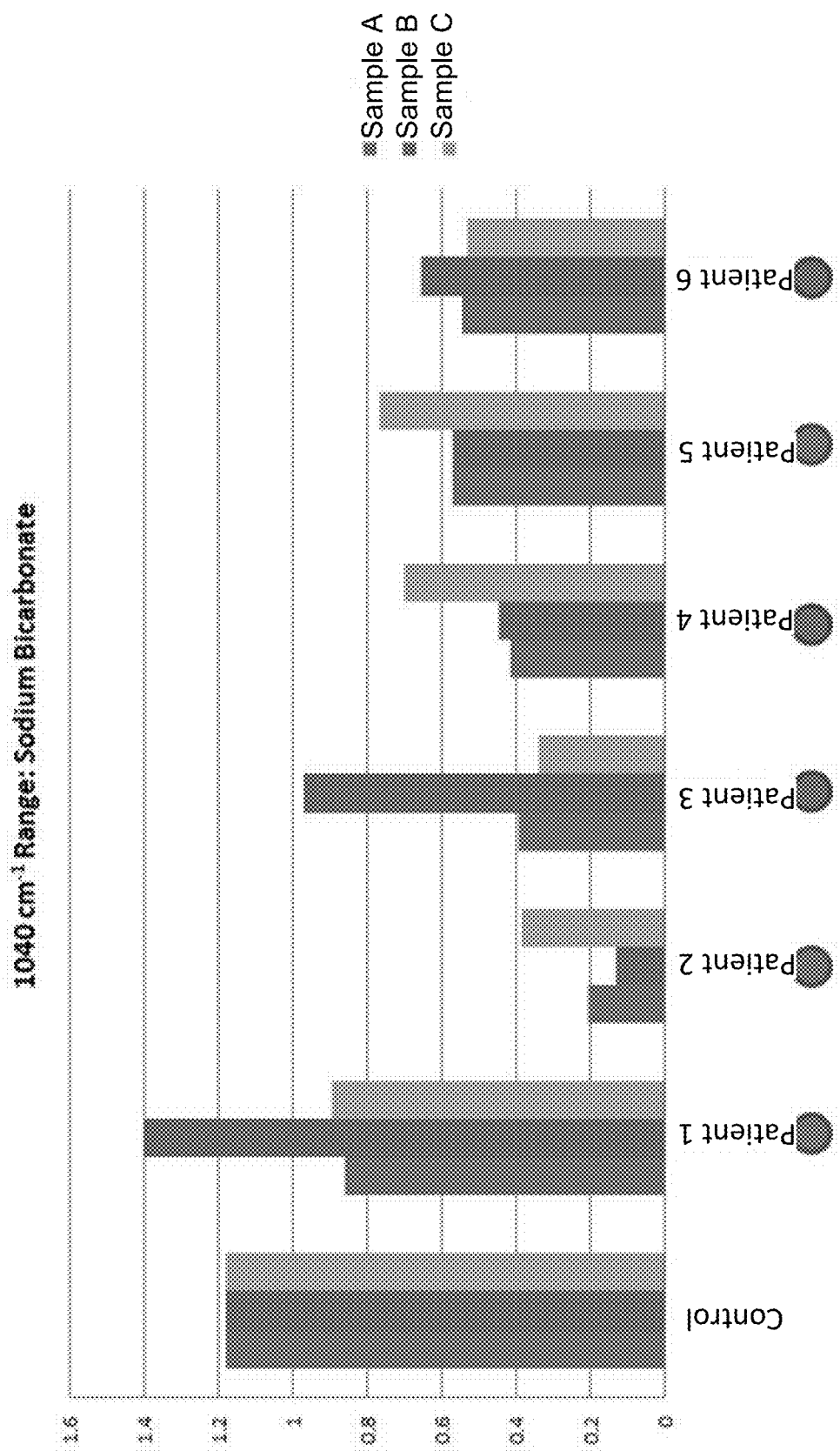

FIGS. 14-20 show the kinetics of different target analyte clearances over the three time points during the hemodialysis treatment for each of the six patients, with FIGS. 14A and 14B comparing urea clearances with that of creatinine, FIG. 15 showing carbohydrate modulation, FIG. 16 showing low MW triglyceride clearances, FIG. 17 showing glycine secretion, FIG. 18 showing aspartic acid/asparagine modulation, FIG. 19 showing glutamic acid/glutamine modulation, and FIG. 20 showing sodium bicarbonate secretion. A takeaway point from these figures is that the clearance patterns of the target analytes over the three time points differed between patients and were thus highly patient-specific.

Figure 21:
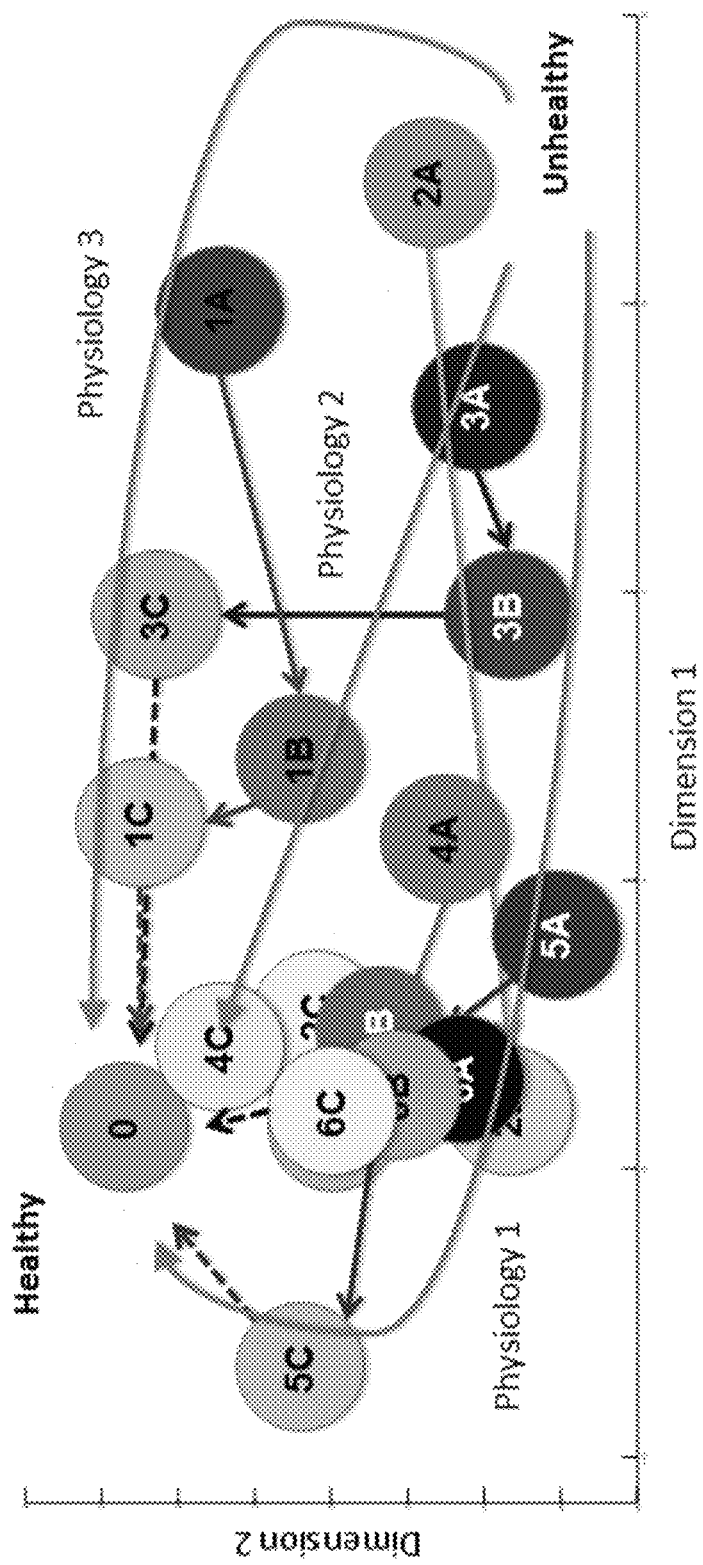
FIG. 21 is a graph showing that chemometric analysis of Raman spectra indicated that the six patients have different starting/finish points and paths.
Figure 22:
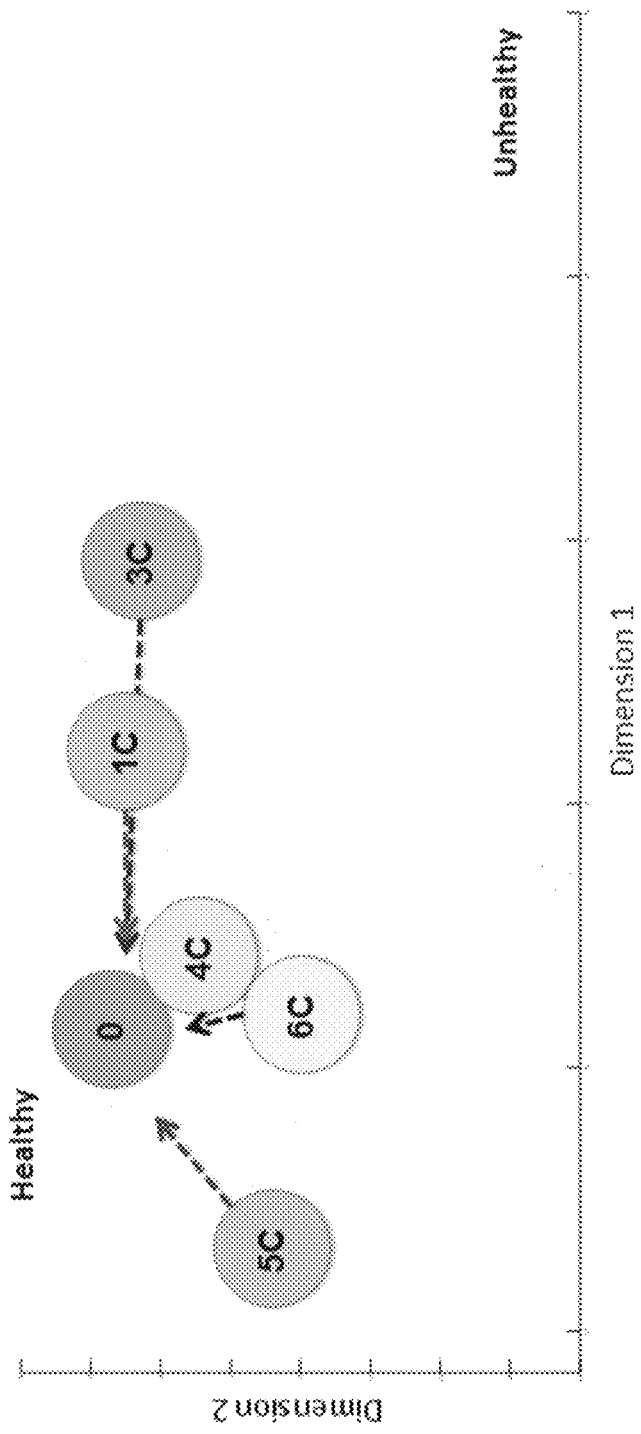
FIG. 22 is a graph showing chemometric analysis of just the finishing points, indicating that the patient's kinetics tend to converge toward the healthy control, yet all six patients finished treatment with a different physiology.

FIG. 21 shows that the above chemometric (or "fingerprint") analysis of Raman spectra showed that the six patients have different starting/finish points and paths. FIG. 22 shows just the finishing points, indicating that the patient's kinetics tend to converge toward the healthy control, yet all six patients finished treatment with a different physiology.

In summary, the results of the Example show that 1) the presence of multiple, diverse target analytes can be measured with Raman spectrometry from dialysate from hemodialysis patients over a course of a dialysis treatment, 2) the kinetics of these analytes over treatment can be followed, 3) the kinetics tends to be patient-specific indicating physiological differences between patients over the course of treatment, 4) the kinetics tend to converge toward a healthy control, although physiological differences remained at the end of treatment. Thus, the results show that measuring target analytes in the dialysate of individual patients can be used to inform patient-specific dialysis prescriptions based on the kinetics of target analytes. For example, the kinetics of individual target analytes may suggest 1) longer or shorter dialysis treatment times, 2) increasing or decreasing the rate of blood flow through the dialyzer, and/or 3) increasing or decreasing the frequency of dialysis treatments. A skilled artisan (e.g. expert clinician) would be able to determine a patient-specific dialysis prescription based on the kinetics of the target analytes.

The present invention has been described with reference to particular embodiments having various features. In light of the disclosure provided above, it will be apparent to those skilled in the art that various modifications and variations can be made in the practice of the present invention without departing from the scope or spirit of the invention. One skilled in the art will recognize that the disclosed features may be used singularly, in any combination, or omitted based on the requirements and specifications of a given application or design. When an embodiment refers to "comprising" certain features, it is to be understood that the embodiments can alternatively "consist of" or "consist essentially of" any one or more of the features. Other embodiments of the invention will be apparent to those skilled in the art from consideration of the specification and practice of the invention.

It is noted in particular that where a range of values is provided in this specification, each value between the upper and lower limits of that range is also specifically disclosed. The upper and lower limits of these smaller ranges may independently be included or excluded in the range as well. The singular forms "a," "an," and "the" include plural referents unless the context clearly dictates otherwise. It is intended that the specification and examples be considered as exemplary in nature and that variations that do not depart from the essence of the invention fall within the scope of the invention. Further, all of the references cited in this disclosure are each individually incorporated by reference herein in their entireties and as such are intended to provide an efficient way of supplementing the enabling disclosure of this invention as well as provide background detailing the level of ordinary skill in the art.

The invention claimed is:
1. A method comprising:
subjecting a patient to an initial dialysis treatment;
obtaining multiple urine and/or dialysate samples associated with the patient;

providing a Raman spectrum for each of the multiple samples associated with the patient;

detecting a molecular fingerprint of four or more analytes relative to one another in each of the Raman spectra and therefrom establishing analyte clearance kinetics indicative of progress of the dialysis treatment; and treating the patient with one or more subsequent dialysis treatment(s) dependent on a disease state associated with the analyte clearance kinetics represented from the multiple samples of the patient;

wherein the subsequent dialysis treatment(s) is/are:
modified relative to the initial dialysis treatment; and
performed for a time, rate, and/or frequency based on the analyte clearance kinetics.

2. The method of claim 1, wherein the samples are taken at the beginning, middle, and end of the initial dialysis treatment.

3. The method of claim 1, wherein the multiple samples are dialysate samples.

4. The method of claim 1, wherein the analytes are chosen from one or more of creatinine, uric acid, uric acid based compounds, interleukin-8, bilirubin, a1-anti-trypsin, arginine, homoarginine, urea, urea-based compounds, urea nitrogen based compounds, ammonium-based compounds, nitrogen-based compounds, vitamins, vitamin C, vitamin B12, folic acid, zinc, amino acids, proteins, nucleic acids, pharmaceutical compounds, 2-heptanal, 2-hexenal, 2-nonenal, 4-decenal, 4-HO-decenal, 4-HO-hexenal, 4-HO-nonenal, 4-HO-octenal, 4 pyrididone-3-carboxy-1-β-D-ribonucleoside, 8-Hydroxy-2'deoxyguanosine, α Keto δ guanidinovlaeric acid, antranilic acid, argininic acid, dimethylarginine, cysteine, decanal, dimethylamine, ethylamine, guanidine, guanidinoacetic acid, guanidine succinic acid, hepatanal, hexanal, hypoxanthine, malondialdehyde, methylguanidine, monomethylamine, neopterine, nicotinamide, N methyl-2-pyridone-5-carboxamide, N-methyl-4-pyridone-3-carboxamide, nonanal, noradrenaline, oxalate, phenylacetic acid, dimethylarginine, trimethylamine, trimethylamine-N-oxide, 3 carboxy-4-methyl-5-propyl-2-furanpropanoic acid, acrolein, carboxymethyllysine, dihydroxyphenylalanine, hippuric acid, homocysteine, indicant, indole-3-acetic acid, indoxyl sulfate, indoxyl-β-D-glucoronide, kynurenic acid, p-cresyl sulfate, pentosidine, phenol, putrescine, permidine, thiocyanate, α1-acid glycoprotein, α1-microglobulin, β-trace protein, β2 microglobulin, adiponectin, angiogenin, calcitonin, complement factor D, cystatin C, fibroblast growth factor-23, glutathione, reduced glutathione, insulin-like growth factor 1 (IGF-1), interleukin 6 (IL-6), interleukin 8 (IL-8), interleukin 10 (IL-10), leptin, myoglobin, osteocalcin, parathyroid hormone (PTH), prolactin, resistin, retinal binding protein, soluble intracellular adhesion molecule-1, tumor necrosis factor α (TNF-α), and vascular endothelial growth factor.

5. The method of claim 1, wherein the treating involves hemodialysis.

6. The method of claim 1, wherein the treating involves peritoneal dialysis.

7. The method of claim 1, wherein one or more of the multiple samples is a waste dialysate.

8. The method of claim 1, wherein the analytes comprise urea, urea-based compounds, urea nitrogen based compounds, sodium bicarbonate, glucose, fatty acids, triglycerides, and/or carbohydrates.

9. The method of claim 1, wherein the analyte clearance kinetics are based on peaks of interest disposed at wavelengths of about 930 $cm^{-1}$, about 1000 $cm^{-1}$, about 1040 $cm^{-1}$, and/or about 1070 $cm^{-1}$.

10. The method of claim 1, wherein the analyte clearance kinetics are based on changes over time of one or more of the four analytes relative to one another.

11. The method of claim 1, wherein the samples are taken at different times.

12. The method of claim 1, wherein the modifying of the subsequent dialysis treatment(s) comprises one or more of:
increasing or decreasing dialysis treatment time; and/or
increasing or decreasing the rate of blood flow through a dialyzer; and/or
increasing or decreasing the frequency of dialysis treatments.

* * * * *